United States Patent [19]
Cody et al.

[11] Patent Number: 5,641,752
[45] Date of Patent: Jun. 24, 1997

[54] METHODS OF USING ENDOTHELIN ANTAGONISTS

[75] Inventors: Wayne Livingston Cody, Saline; Patricia DePue, Canton; Annette Marian Doherty, Ann Arbor; John Xiaoqiang He, Ypsilanti; Michael Douglas Taylor, Ann Arbor, all of Mich.

[73] Assignee: Warner-Lambert Company, Morris Plains, N.J.

[21] Appl. No.: 316,533

[22] Filed: Sep. 30, 1994

Related U.S. Application Data

[60] Division of Ser. No. 995,480, Dec. 21, 1992, Pat. No. 5,382,569, which is a continuation-in-part of Ser. No. 809,746, Dec. 18, 1991, abandoned, which is a continuation-in-part of Ser. No. 701,274, May 16, 1991, abandoned.

[51] Int. Cl.$^6$ .............................. A61K 38/00; C07K 5/00; C07K 7/00
[52] U.S. Cl. ................................. 514/17; 530/329
[58] Field of Search ............................. 514/17; 530/329

[56] References Cited

FOREIGN PATENT DOCUMENTS

| WO9220706 | 11/1992 | WIPO. |
| WO9316104 | 8/1993 | WIPO. |
| WO9321219 | 10/1993 | WIPO. |

OTHER PUBLICATIONS

PCT International Search Report for Corresponding PCT Application—PCT/US 93/12377 Which Was Filed Dec. 17, 1993.

Chemical Abstracts, vol. 117, No. 13, Sep. 28, 1992, W.L. Cody, et al., J. Med. Chem. 1992, 35 (17), 3301–3303.

G.R. Pettit, "Synthetic Peptides", 1970, Van Nostrand Reinhold Company, p. 149.

Rovero, P., et al., British Journal of Pharmacology 101, pp. 232–234.

Doherty, A. M., et al., Abstract, Second International Conference on Endothelin, Dec. 9, 1990.

J. of Cardiovascular Pharmacology 17 (Suppl. 7) S59–S61, 1991, A. M. Doherty, et al. "Structure–Activity Studies of the C–Terminal Region of the Endothelins and the Sarafotoxins".

PCT International Search Report for Corresponding PCT Application No. PCT/US 92/03408 Filed Apr. 24, 1992.

Biochemical & Biophysical Research Comm., vol. 163, No. 1, Aug. 30, 1989, K. Nakajima, pp. 424–429.

1992 FASEB Meeting, Anaheim California, Apr. 5–9, 1992, 390, D.M. LaDouceur, et al.

*Primary Examiner*—Avis M. Davenport
*Attorney, Agent, or Firm*—Francis J. Tinney

[57] ABSTRACT

Novel antagonists of endothelin are described, as well as methods for the preparation and pharmaceutical compositions of the same, which are useful in treating elevated levels of endothelin, acute and chronic renal failure, hypertension, myocardial infarction, metabolic, endocrinological, neurological disorders, congestive heart failure, endotoxic shock, subarachnoid hemorrhage, arrhythmias, asthma, preeclampsia, Raynaud's disease, percutaneous transluminal coronary angioplasty or restenosis, angina, cancer, pulmonary hypertension, ischemic disease, gastric mucosal damage, ischemic bowel disease, and diabetes.

5 Claims, No Drawings

METHODS OF USING ENDOTHELIN ANTAGONISTS

This is a divisional of U.S. application Ser. No. 07/995,480 filed Dec. 21, 1992, now U.S. Pat. No. 5,392,569 which is a continuation-in-part of U.S. application Ser. No. 07/809,746 filed Dec. 18, 1991, now abandoned, which is a continuation-in-part of U.S. application Ser. No. 07/701,274 filed May 16, 1991 and now abandoned.

BACKGROUND OF THE INVENTION

The present invention relates to novel antagonists of endothelin useful as pharmaceutical agents, to methods for their production, to pharmaceutical compositions which include these compounds and a pharmaceutically acceptable carrier, and to pharmaceutical methods of treatment. More particularly, the novel compounds of the present invention are antagonists of endothelin useful in treating elevated levels of endothelin, acute and chronic renal failure, hypertension, myocardial infarction, metabolic, endocrinological, neurological disorders, congestive heart failure, endotoxic shock, subarachnoid hemorrhage, arrhythmias, asthma, preeclampsia, Raynaud's disease, percutaneous transluminal coronary angioplasty and restenosis, angina, cancer, pulmonary hypertension, ischemic disease, gastric mucosal damage, ischemic bowel disease, and diabetes.

Endothelin-1 (ET-1), a potent vasoconstrictor, is a 21 amino acid bicyclic peptide that was first isolated from cultured porcine aortic endothelial cells. Endothelin-1, is one of a family of structurally similar bicyclic peptides which include; ET-2, ET-3, vasoactive intestinal contractor (VIC), and the sarafotoxins (SRTX's). The unique bicyclic structure and corresponding arrangement of the disulfide bridges of ET-1, which are the same for the endothelins, VIC, and the sarafotoxins, has led to significant speculation as to the importance of the resulting induced secondary structure to receptor binding and functional activity. ET-1 analogues with incorrect disulfide pairings exhibit at least 100-fold less vasoconstrictor activity. The flexible C-terminal hexapeptide of ET-1 has been shown to be important for binding to the ET receptor and functional activity in selected tissues. Additionally, the C-terminal amino acid (Trp-21) has a critical role in binding and vasoconstrictor activity, since ET[1–20] exhibits approximately 1000-fold less functional activity.

Endothelin is involved in many human disease states.

Several in vivo studies with ET antibodies have been reported in disease models. Left coronary artery ligation and reperfusion to induce myocardial infarction in the rat heart, caused a four- to sevenfold increase in endogenous endothelin levels. Administration of ET antibody was reported to reduce the size of the infarction in a dose-dependent manner (Watanabe, T., et al, "Endothelin in Myocardial Infarction," Nature (Lond.) 344:114 (1990)). Thus, ET may be involved in the pathogenesis of congestive heart failure and myocardial ischemia (Margulies, K. B., et al, "Increased Endothelin in Experimental Heart Failure," Circulation 82:2226 (1990)).

Studies by Kon and colleagues using anti-ET antibodies in an ischemic kidney model, to deactivate endogenous ET, indicated the peptide's involvement in acute renal ischemic injury (Kon, V., et al, "Glomerular Actions of Endothelin In Vivo," J. Clin. Invest. 83:1762 (1989)). In isolated kidneys, preexposed to specific antiendothelin antibody and then challenged with cyclosporine, the renal perfusate flow and glomerular filtration rate increased, while renal resistance decreased as compared with isolated kidneys preexposed to a nonimmunized rabbit serum. The effectiveness and specificity of the anti-ET antibody were confirmed by its capacity to prevent renal deterioration caused by a single bolus dose (150 pmol) of synthetic ET, but not by infusion of angiotensin II, norepinephrine, or the thromboxane $A_2$ mimetic U-46619 in isolated kidneys (Perico, N., et al, "Endothelin Mediates the Renal Vasoconstriction Induced by Cyclosporine in the Rat," J. Am. Soc. Nephrol. 1:76 (1990)).

Others have reported inhibition of ET-1 or ET-2-induced vasoconstriction in rat isolated thoracic aorta using a monoclonal antibody to ET-1 (Koshi, T., et al, "Inhibition of Endothelin (ET)-I and ET-2-Induced Vasoconstriction by Anti-ET-1 Monoclonal Antibody," Chem. Pharm. Bull., 39:1295 (1991)).

Combined administration of ET-1 and ET-1 antibody to rabbits showed significant inhibition of the BP and renal blood flow responses (Miyamori, I., et al, "Systemic and Regional Effects of Endothelin in Rabbits: Effects of Endothelin Antibody," Clin. Exp. Pharmacol. Physiol., 17:691 (1990)).

Other investigators have reported that infusion of ET-specific antibodies into spontaneously hypertensive rats (SHR) decreased mean arterial pressure (MAP), and increased glomerular filtration rate and renal blood flow. In the control study with normotensive Wistar-Kyoto rats (WKY) there were no significant changes in these parameters (Ohno, A. "Effects of Endothelin-Specific Antibodies and Endothelin in Spontaneously Hypertensive Rats," J. Tokyo Women's Med. Coll., 61:951 (1991)).

In addition, elevated levels of endothelin have been reported in several disease states (see Table I below).

Burnett and co-workers recently demonstrated that exogenous infusion of ET (2.5 ng/kg/mL) to anesthetized dogs, producing a doubling of the circulating concentration, did have biological actions (Lerman, A., et al, "Endothelin has Biological Actions at Pathophysiological Concentrations," Circulation 83:1808 (1991)). Thus heart rate and cardiac output decreased in association with increased renal and systemic vascular resistances and antinatriuresis. These studies support a role for endothelin in the regulation of cardiovascular, renal, and endocrine function.

In the anesthetized dog with congestive heart failure, a significant two- to threefold elevation of circulating ET levels has been reported (Cavero, P. G., et al, "Endothelin in Experimental Congestive Heart Failure in the Anesthetized Dog," Am. J. Physiol. 259:F312 (1990)), and studies in humans have shown similar increases (Rodeheffer, R. J., et al, "Circulating Plasma Endothelin Correlates With the Severity of Congestive Heart Failure in Humans," Am. J. Hypertension 4:9A (1991)). When ET was chronically infused into male rats, to determine whether a long-term increase in circulating ET levels would cause a sustained elevation in mean arterial blood pressure, significant, sustained, and dose-dependent increases in mean arterial BP were observed. Similar results were observed with ET-3 although larger doses were required (Mortenson, L. H., et al, "Chronic Hypertension Produced by Infusion of Endothelin in Rats," Hypertension, 15:729 (1990)).

The distribution of the two cloned receptor subtypes, termed $ET_A$ and $ET_B$, have been studied extensively (Arai, H., et al, Nature 348:730 (1990), Sakurai, T., et al, Nature 348:732 (1990)). The $ET_A$, or vascular smooth muscle receptor, is widely distributed in cardiovascular tissues and in certain regions of the brain (Lin, H. Y., et al, Proc. Natl.

Acad. Sci. 88:3185 (1991)). The $ET_B$ receptor, originally cloned from rat lung, has been found in rat cerebellum and in endothelial cells, although it is not known if the $ET_B$ receptors are the same from these sources. The human ET receptor subtypes have been cloned and expressed (Sakamoto, A., et al, Biochem. Biophys. Res. Chem. 178:656 (1991), Hosoda, K., et al, FEBS Lett. 287:23 (1991)). The $ET_A$ receptor clearly mediates vasoconstriction and there have been a few reports implicating the $ET_B$ receptor in the initial vasodilatory response to ET (Takayanagi, R., et al, FEBS Lett. 282:103 (1991)). However, recent data has shown that the $ET_B$ receptor can also mediate vasoconstriction in some tissue beds (Panek, R. L., et al, Biochem. Biophys. Res. Commun. 183(2):566 (1992)).

Comparison of the receptor affinities of the ET's and SRTX's in rats and atria ($ET_A$) or cerebellum and hippocampus ($ET_B$), indicate that SRTX-c is a selective $ET_B$ ligand (Williams, D. L., et al, Biochem. Biophys. Res. Commun., 175:556 (1991)). A recent study showed that selective $ET_B$ agonists caused only vasodilation in the rat aortic ring, possibly through the release of EDRF from the endothelium (ibid). Thus, reported selective $ET_B$ agonists, for example, the linear analog ET[1,3,11,15-Ala] and truncated analogs ET[6-21, 1,3,11,15-Ala], ET[8-21,11,15-Ala], and N-Acetyl-ET[10-21,11,15-Ala] caused vasorelaxation in isolated, endothelium-intact porcine pulmonary arteries (Saeki, T., et al, Biochem. Biophys. Res. Commun. 179:286 (1991)). However, some ET analogs are potent vasoconstrictors in the rabbit pulmonary artery, a tissue that appears to possess an $ET_B$ y, nonselective type of receptor (ibid).

Plasma endothelin-1 levels were dramatically increased in a patient with malignant hemangioendothelioma (K. Nakagawa et al, Nippon Hifuka Gakkai Zasshi, 1990, 100, 1453–1456).

The ET receptor antagonist BQ-123 has been shown to block ET-1 induced bronchoconstriction and tracheal smooth muscle contraction in allergic sheep providing evidence for expected efficacy in bronchopulmonary diseases such as asthma (Noguchi, et al, Am. Rev. Respir. Dis., 1992, 145 (4 Part 2), A858).

Circulating endothelin levels are elevated in women with preeclampsia and correlate closely with serum uric acid levels and measures of renal dysfunction. These observations indicate a role for ET in renal constriction in preeclampsia (Clark B. A., et al, Am. J. Obstet. Gynecol., 1992, 166, 962–968).

Plasma immunoreactive endothelin-1 concentrations are elevated in patients with sepsis and correlate with the degree of illness and depression of cardiac output (Pittett J., et al, Ann Surg., 1991, 213(3), 262).

In addition the ET-1 antagonist BQ-123 has been evaluated in a mouse model of endotoxic shock. This $ET_A$ antagonist significantly increased the survival rate in this model (Toshiaki M., et al, 20.12.90. EP 0 436 189 A1).

Endothelin is a potent agonist in the liver eliciting both sustained vasoconstriction of the hepatic vasculature and a significant increase in hepatic glucose output (Gandhi C. B., et al, Journal of Biological Chemistry, 1990, 265(29), 17432). In streptozotocin-diabetic rats there is an increased sensitivity to endothelin-1 (Tammesild P. J., et al, Clin. Exp. Pharmacol. Physiol., 1992, 19(4), 261). In addition increased levels of plasma ET-1 have been observed in microalbuminuric insulin-dependent diabetes mellitus patients indicating a role for ET in endocrine disorders such as diabetes (Collier A., et al, Diabetes Care, 1992, 15(8), 1038).

$ET_A$ antagonist receptor blockade has been found to produce an antihypertensive effect in normal to low renin models of hypertension with a time course similar to the inhibition of ET-1 pressor responses (Basil M. K., et al, J. Hypertension, 1992, 10 (Suppl 4), S49). The endothelins have been shown to be arrhythmogenic, and to have positive chronotropic and inotropic effects, thus ET receptor blockade would be expected to be useful in arrhythmia and other cardiovascular disorders (Han S. -P., et al, Life Sci., 1990, 46, 767).

The widespread localization of the endothelins and their receptors in the central nervous system and cerebrovascular circulation has been described (Nikolov R. K., et al, Drugs of Today, 1992, 28(5), 303–310). Intracerebroventricular administration of ET-1 in rats has been shown to evoke several behavioral effects. These factors strongly suggest a role for the ETs in neurological disorders. The potent vasoconstrictor action of ETs on isolated cerebral arterioles suggests the importance of these peptides in the regulation of cerebrovascular tone. Increased ET levels have been reported in some CNS disorders, i.e., in the CSF of patients with subarachnoid hemorrhage and in the plasma of women with preeclampsia. Stimulation with ET-3 under conditions of hypoglycemia have been shown to accelerate the development of striatal damage as a result of an influx of extracellular calcium. Circulating or locally produced ET has been suggested to contribute to regulation of brain fluid balance through effects on the choroid plexus and CSF production. ET-1 induced lesion development in a new model of local ischemia in the brain has been described.

Circulating and tissue endothelin immunoreactivity is increased more than twofold in patients with advanced atherosclerosis (A. Lerman, et al, New England J. Med., 1991, 325, 997–1001). Increased endothelin immunoreactivity has also been associated with Buerger's disease (K. Kanno, et al, J. Amer. Med. Assoc., 1990, 264, 2868) and Raynaud's phenomenon (M. R. Zamora, et al, Lancet, 1990, 336, 1144–1147). Likewise, increased endothelin concentrations were observed in hypercholesterolemic rats (T. Horio, et al, Atherosclerosis, 1991, 89, 239–245).

An increase of circulating endothelin levels was observed in patients that underwent percutaneous transluminal coronary angioplasty (PTCA) (A. Tahara, et al, Metab. Clino Exp., 1991, 40, 1235–1237, K. Sanjay, et al, Circulation, 1991, 84(Suppl. 4), 726).

Increased plasma levels of endothelin have been measured in rats (T. J. Stelzner, et al, Am. J. Physiol., 1992, 262, L614–L620) and individuals (T. Miyauchi, et al, Jpn. J. Pharmacol., 1992, 58, 279P, D. J. Stewart, et al, Ann. Internal Medicine, 1991, 114 464–469) with pulmonary hypertension.

Elevated levels of endothelin have also been measured in patients suffering from ischemic heart disease (M. Yasuda, et al, Amer. Heart J., 1990, 119 801–806, S. G. Ray, et al, Br. Heart J., 1992, 67, 383–386) and either stable or unstable angina (J. T. Stewart, et al, Br. Heart J., 1991, 66, 7–9).

Infusion of an endothelin antibody 1 h prior to and 1 h after a 60 minute period of renal ischaemia resulted in changes in renal function versus control. In addition, an increase in glomerular platelet-activating factor was attributed to endothelin (A. Lopez-Farre, et al, J. Physiology, 1991, 444, 513– 522). In patients with chronic renal failure as well as in patients on regular hemodialysis treatment mean plasma endothelin levels were significantly increased (F. Stockenhuber, et al, Clin. Sci. (Lond.), 1992, 82, 255–258). In addition it has been suggested that the proliferative effect of endothelin on mesangial cells may be a contributing factor in chronic renal failure (P. J. Schultz, *J. Lab. Clin. Med.*, 1992, 119, 448–449).

Local intra-arterial administration of endothelin has been shown to induce small intestinal mucosal damage in rats in a dose-dependent manner (S. Mirua, et al, *Digestion*, 1991, 48, 163–172). Administration of endothelin-1 in the range of 50–500 pmol/kg into the left gastric artery increased the tissue type plasminogen activator release and platelet activating formation, and induced gastric mucosal haemorrhagic change in a dose dependent manner (I. Kurose, et al, *Gut*, 1992, 33, 868–871). Furthermore, it has been shown that an anti-ET-1 antibody reduced ethanol-induced vasoconstriction in a concentration-dependent manner (E. Masuda, et al, *Am. J. Physiol.*, 1992, 262, G785–G790). Elevated endothelin levels have been observed in patients suffering from Crohn's disease and ulcerative colitis (S. H. Murch, et al, *Lancet*, 1992, 339, 381–384).

TABLE I

Plasma Concentrations of ET-1 in Humans

| Condition | Normal Control | ET Plasma Levels Reported (pg/mL) |
|---|---|---|
| Atherosclerosis | 1.4 | 3.2 pmol/L |
| Surgical operation | 1.5 | 7.3 |
| Buerger's disease | 1.6 | 4.8 |
| Takayasu's arteritis | 1.6 | 5.3 |
| Cardiogenic shock | 0.3 | 3.7 |
| Congestive heart failure (CHF) | 9.7 | 20.4 |
| Mild CHF | 7.1 | 11.1 |
| Severe CHF | 7.1 | 13.8 |
| Dilated cardiomyopathy | 1.6 | 7.1 |
| Preeclampsia | 10.4 pmol/L | 22.6 pmol/L |
| Pulmonary hypertension | 1.45 | 3.5 |
| Acute myocardial infarction | 1.5 | 3.3 |
| (several reports) | 6.0 | 11.0 |
| | 0.76 | 4.95 |
| | 0.50 | 3.8 |
| Subarachnoid hemorrhage | 0.4 | 2.2 |
| Crohn's Disease | 0–24 fmol/mg | 4–64 fmol/mg |
| Ulcerative colitis | 0–24 fmol/mg | 20–50 fmol/mg |
| Cold pressor test | 1.2 | 8.4 |
| Raynaud's phenomenon | 1.7 | 5.3 |
| Raynaud's/hand cooling | 2.8 | 5.0 |
| Hemodialysis | <7 | 10.9 |
| (several reports) | 1.88 | 4.59 |
| Chronic renal failure | 1.88 | 10.1 |
| Acute renal failure | 1.5 | 10.4 |
| Uremia before hemodialysis | 0.96 | 1.49 |
| Uremia after hemodialysis | 0.96 | 2.19 |
| Essential hypertension | 18.5 | 33.9 |
| Sepsis syndrome | 6.1 | 19.9 |
| Postoperativecardiac | 6.1 | 11.9 |
| Inflammatory arthritides | 1.5 | 4.2 |
| Malignant hemangio-endothelioma | 4.3 | 16.2 (after removal) |

Rovero, P., et al, *British Journal of Pharmacology* 101, pages 232–236 (1990) disclosed various analogs of the C-terminal hexapeptide of ET-1, none of which were reported to be antagonists of ET-1.

Doherty, A. M., et al, Abstract, Second International Conference on Endothelin, Tsukuba, Japan, Dec. 9, 1990, and the published manuscript (*J. Cardiovasc. Pharm.* 17 (Suppl. 7), 1991, pp. 559–561) disclosed various analogs of the C-terminal hexapeptide of ET-1, none of which exhibited any functional activity.

However, we have surprisingly and unexpectedly found that a series of C-terminal hexapeptide and related analogs of ET-1 are receptor antagonists of endothelin. Additional data for the activity of this series of peptides is found in the following references (W. L. Cody, et al, *J. Med. Chem.*, 1992, 35, 3303., D. M. LaDouceur, et al, FASEB, 1992).

SUMMARY OF THE INVENTION

Accordingly, the present invention is a compound of Formula I

wherein $AA^1$ is

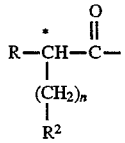

wherein R is hydrogen alkyl, alkenyl, alkynyl, cycloalkyl, cycloalkylalkyl, aryl, heteroaryl, fluorenylmethyl, $$-N-R^3$$
$$\phantom{-N-}R^4$$

wherein $R^3$ and $R^4$ are each the same or different and each is hydrogen, alkyl, alkenyl, alkynyl, cycloalkyl, cycloalkylalkyl, aryl, heteroaryl, or fluorenylmethyl, $-OR^3$ wherein $R^3$ is as defined above,

wherein $R^3$ is as defined above,

wherein $R^3$ and $R^4$ are each the same or different and each is as defined above,

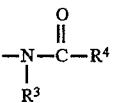

wherein $R^3$ and $R^4$ are each the same or different and each is as defined above, but $R^4$ is not hydrogen,

wherein $R^3$ is as defined above,

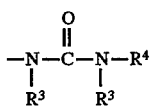

wherein $R^3$ and $R^4$ are defined above,

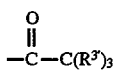

wherein $R^{3'}$ is F, Cl, Br, or I, or $-CH_2OR^3$ wherein $R^3$ is as defined above,
n is zero or an integer of 1, 2, 3, 4, 5, or 6 and
$R^2$ is hydrogen, alkyl, trityl,

wherein $R^3$ and $R^4$ are each the same or different and each is as defined above,

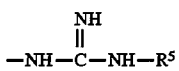

wherein $R^5$ is hydrogen, p-toluenesulfonyl, nitro or

wherein $R^6$ is alkyl, cycloalkyl, aryl, or heteroaryl,

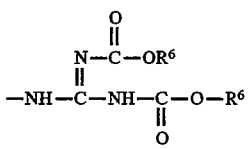

wherein $R^6$ is as defined above,

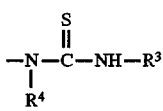

wherein $R^3$ and $R^4$ are each the same or different and each is as defined above, aryl, heteroaryl, or heterocycloalkyl,

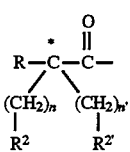

wherein n and n' are each the same or different and each is as defined above for n, $R^2$ and $R^{2'}$ are each the same or different and each is as defined above for $R^2$, and R is as defined above

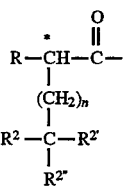

wherein $R^2$, $R^{2'}$, and $R^{2''}$ are each the same or different and each is as defined above for $R^2$, R and n are defined as above,

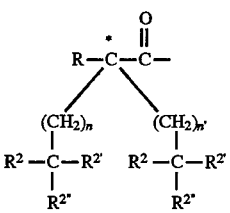

wherein n and n' are each the same or different and each is as defined above for n, $R^2$, $R^{2'}$, and $R^{2''}$ are each the same or different and each is as defined above for $R^2$ and R is as defined above,

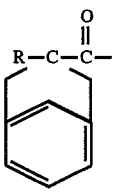

wherein R is as defined above,

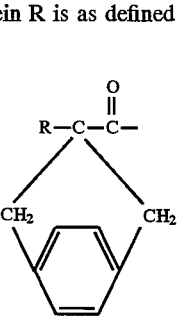

wherein R is as defined above,

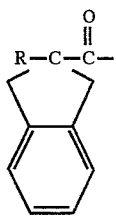

wherein R is as defined above,

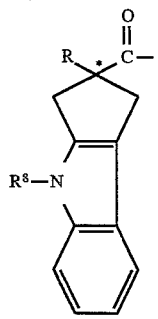

wherein $R^8$ is hydrogen, or alkyl, and R is as defined above,

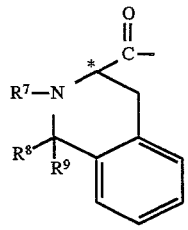

wherein $R^7$ is hydrogen, alkyl, cycloalkyl, aryl, or heteroaryl, $R^8$ and $R^9$ are each the same or different and each is as defined above for $R^8$

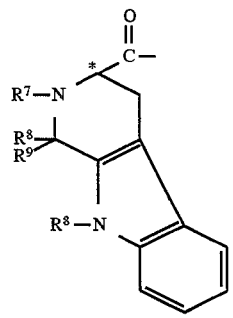

wherein $R^7$, $R^8$, and $R^9$ are as defined above or

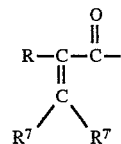

wherein $R^7$ and $R^{7'}$ are each the same or different and is as defined above for $R^7$, and R is as defined above;

$AA^2$, $AA^3$, $AA^4$, and $AA^5$ are each independently absent or each independently

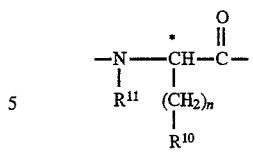

wherein $R^{10}$ is hydrogen, alkyl, aryl, cycloalkyl, alkenyl, alkynyl, $-OR^3$ wherein $R^3$ is as defined above,

wherein $R^3$ and $R^4$ are each the same or different and each is as defined above,

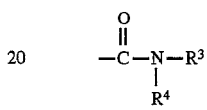

wherein $R^3$ and $R^4$ are each the same or different and each is as defined above,

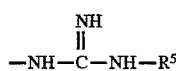

wherein $R^5$ is as defined above, $-S(O)_m R^3$ wherein m is zero or an integer of 1 or 2, and $R^3$ is as defined above where $R^3$ is not hydrogen,

wherein $R^3$ is as defined above,

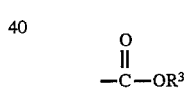

wherein $R^3$ is as defined above,
$R^{11}$ is hydrogen, alkyl, or aryl, and
n is as defined above,

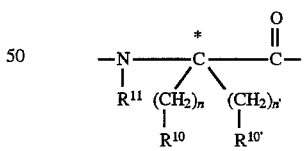

wherein n and n' are each the same or different and each is as defined above for n, $R^{10}$ and $R^{10'}$ are each the same or different and each is as defined above for $R^{10}$, and $R^{11}$ is as defined above,

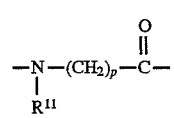

wherein p is an integer of 1, 2, 3, 4, 5, or 6 and $R^{11}$ is as defined above,

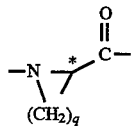

wherein q is zero or an integer of 1, 2, 3, or 4,

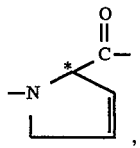

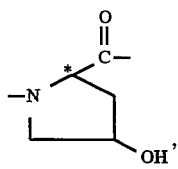

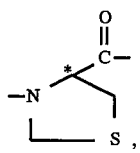

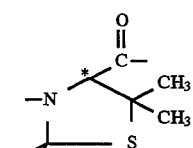

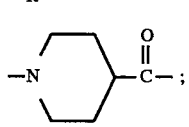

wherein $R^2$ and $R^{2'}$ are each the same or different and each is as defined above for $R^2$, and $AA^6$ is

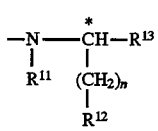

wherein $R^{13}$ is —$(CH_2)_n$—$CO_2H$ wherein n is as defined above, —$(CH_2)_n$—OH wherein n is as defined above, or

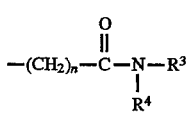

wherein n, $R^3$, and $R^4$ are as defined above,

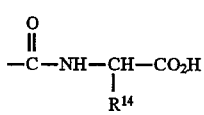

wherein $R^{14}$ is hydrogen or —$CH_2$—$CO_2H$ $R^{12}$ is aryl, heteroaryl, or heterocycloalkyl, and $R^{11}$ and n are as defined above,

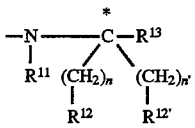

wherein n and n' are each the same or different and each is as defined above for n, and $R^{12}$ and $R^{12'}$ are each the same or different and each is as defined above for $R^{12}$ and $R^{11}$, and $R^{13}$ are as defined above,

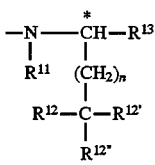

wherein $R^{12}$, $R^{12'}$, and $R^{12''}$ are each the same or different and each is as defined above for $R^{12}$ and $R^{11}$, $R^{13}$ and n are as defined above,

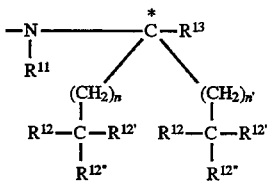

wherein n and n' are each the same or different and each is as defined above for n, $R^{12}$, $R^{12'}$, and $R^{12''}$ are each the same or different and each is as defined above for $R^{12}$, and $R^{11}$ and $R^{13}$ are as defined above,

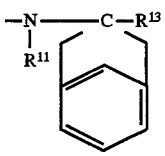

wherein $R^{11}$ and $R^{13}$ are as defined above,

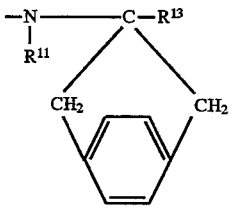

wherein $R^{11}$ and $R^{13}$ are as defined above,

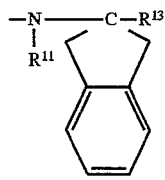

wherein $R^{11}$ and $R^{13}$ are as defined above,

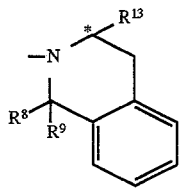

wherein $R^8$ and $R^9$ are each the same or different and each is as defined above for $R^8$ and $R^9$, and $R^{13}$ is as defined above,

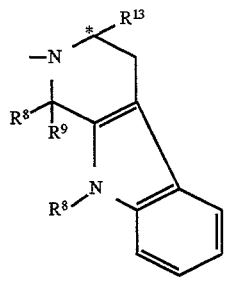

wherein $R^8$ and $R^9$ are each the same or different and each is as defined above for $R^s$ and $R^9$, and $R^{13}$ is as defined above,

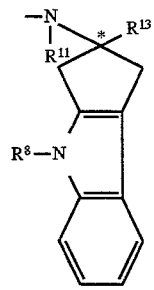

wherein $R^8$, $R^{11}$, and $R^{13}$ are as defined above, and

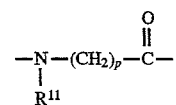

wherein $R^{11}$ and p are as defined above;

stereochemistry at $\overset{*}{c}H$ or $\overset{*}{c}$ in $AA^1$ is D, stereochemistry at $\overset{*}{c}H$ or $\overset{*}{c}$ in $AA^2$, $AA^3$, $AA^4$, or $AA^5$ is D, L, or DL and stereochemistry at $\overset{*}{c}H$ or $\overset{*}{c}$ in $AA^6$ is L; and with the exclusion of the compounds wherein $AA^1$ is

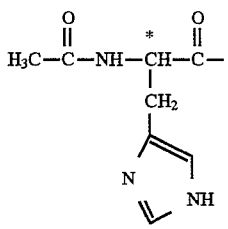

wherein $\overset{*}{c}H$ is D stereochemistry, or

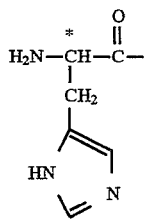

wherein $\overset{*}{c}H$ is D stereochemistry, $AA^2$ is

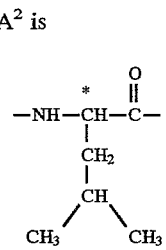

wherein $\overset{*}{c}H$ is L stereochemistry, $AA^3$ is

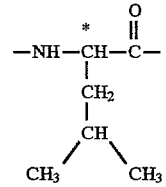

wherein $\overset{*}{c}H$ is L stereochemistry, $AA^4$ and $AA^5$ are each

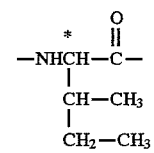

wherein $\overset{*}{c}H$ is L stereochemistry, and

AA⁶ is $$-NH-\overset{*}{C}H-\overset{O}{\underset{\|}{C}}-OH$$
$$\underset{\underset{H}{\overset{|}{N}}}{\overset{|}{\underset{}{CH_2}}}\text{-(indole)}$$

wherein $\overset{*}{c}H$ is L stereochemistry; or a pharmaceutically acceptable salt thereof.

Elevated levels of endothelin have been postulated to be involved in a number of pathophysiological states including diseases associated with the cardiovascular system as well as various metabolic and endocrinological disorders. As antagonists of endothelin, the compounds of Formula I are useful in the treatment of elevated levels of endothelin, acute and chronic renal failure, hypertension, myocardial infarction, metabolic, endocrinological and neurological disorders, congestive heart failure, endotoxic shock, subarachnoid hemorrhage, arrhythmias, asthma, preeclampsia, Raynaud's disease, percutaneous transluminal coronary angioplasty and restenosis, angina, cancer, pulmonary hypertension, ischemic disease, gastric mucosal damage, ischemic bowel disease, and diabetes.

A still further embodiment of the present invention is a pharmaceutical composition for administering an effective amount of a compound of Formula I in unit dosage form in the treatment methods mentioned above.

Finally, the present invention is directed to methods for production of a compound of Formula I.

DETAILED DESCRIPTION OF THE INVENTION

In the compounds of Formula I, the term "alkyl" means a straight or branched hydrocarbon radical having from 1 to 12 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl, undecyl, dodecyl, and the like.

The term "alkenyl" means a straight or branched unsaturated hydrocarbon radical having from 2 to 12 carbon atoms and includes, for example, ethenyl, 2-propenyl, 1-butenyl, 2-butenyl, 1-pentenyl, 2-pentenyl, 3-methyl-3-butenyl, 1-hexenyl, 2-hexenyl, 3-hexenyl, 3-heptenyl, 1-octenyl, 1-nonenyl, 1-decenyl, 1-undecenyl, 1-dodecenyl, and the like.

The term "alkynyl" means a straight or branched triple bonded unsaturated hydrocarbon radical having from 2 to 12 carbon atoms and includes, for example, ethynyl, 2-propynyl, 1-butynyl, 2-butynyl, 3-butynyl, 1-pentynyl, 3-pentynyl, 1-hexynyl, 2-hexynyl, 3-hexynyl, 3-heptynyl, 1-octynyl, 2-octynyl, 1-nonynyl, 2-nonynyl, 3-nonynyl, 4-nonynyl, 1-decynyl, 2-decynyl, 2-undecynyl, 3-undecynyl, 3-dodecynyl, and the like.

The term "cycloalkyl" means a saturated hydrocarbon ring which contains from 3 to 12 carbon atoms, for example, cyclopropyl, cyclobutyl, cyclopentyl, cyclohexyl, adamantyl, and the like.

The term "cycloalkylalkyl" means a saturated hydrocarbon ring attached to an alkyl group wherein alkyl is as defined above. The saturated hydrocarbon ring contains from 3 to 12 carbon atoms. Examples of such are cyclopropylmethyl, cyclopentylmethyl, cyclohexylmethyl, adamantylmethyl and the like.

The terms "alkoxy" and "thioalkoxy" are O-alkyl or S-alkyl as defined above for alkyl.

The term "aryl" means an aromatic radical which is a phenyl group, a benzyl group, a naphthyl group, a biphenyl group, a pyrenyl group, an anthracenyl group, or a fluorenyl group and the like, unsubstituted or substituted by 1 to 4 substituents selected from alkyl as defined above, alkoxy as defined above, thioalkoxy as defined above, hydroxy, thiol, nitro, halogen, amino, $$-NH-\overset{O}{\underset{\|}{C}}-alkyl$$

wherein alkyl is as defined above, $$-\overset{O}{\underset{\|}{C}}-O-alkyl$$

wherein alkyl is as defined above, $$-\overset{O}{\underset{\|}{C}}-alkyl$$

wherein alkyl is as defined above, or aryl.

The term "heteroaryl" means a heteroaromatic radical which is 2-or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, or 2-, 4-, 5-, 6-, or 7-benzoxazolyl, 2-, 4-, 5-, 6-, or 7-benzimidazolyl, 2-, 4-, 5-, 6-, or 7-benzothiazolyl, unsubstituted or substituted by 1 to 2 substituents selected from alkyl as defined above, aryl as defined above, alkoxy as defined above, thioalkoxy as defined above, hydroxy, thiol, nitro, halogen, formyl, amino, $$-NH-\overset{O}{\underset{\|}{C}}-alkyl$$

wherein alkyl is as defined above, $$-\overset{O}{\underset{\|}{C}}-O-alkyl$$

wherein alkyl is as defined above, $$-\overset{O}{\underset{\|}{C}}-alkyl$$

wherein alkyl is as defined above or phenyl.

The term "heterocycloalkyl" means 2- or 3-tetrahydrothieno, 2- or 3-tetrahydrofurano, 2- or 3-pyrrolidino, 2-, 4-, or 5-thiazolidino, 2-, 4-, or 5-oxazolidino, 2-, 3-, or 4-piperidino, N-morpholinyl or N-thiamorpholinyl.

"Halogen" is fluorine, chlorine, bromine or iodine.

The following table provides a list of abbreviations and definitions thereof used in the present invention.

TABLE

| Abbreviation* | Amino Acid |
|---|---|
| Ala | Alanine |
| Arg | Arginine |
| Asn | Asparagine |
| Asp | Aspartic acid |
| Cys | Cysteine |
| Glu | Glutamic acid |
| Gln | Gluatmine |
| Gly | Glycine |
| His | Histidine |
| Ile | Isoleucine |
| Leu | Leucine |
| Lys | Lysine |
| Met | Methionine |
| Phe | Phenylalanine |
| Pro | Proline |
| Ser | Serine |
| Thr | Threonine |
| Trp | Tryptophan |
| Tyr | Tyrosine |
| Val | Valine |

| Abbreviation* | Modified and Unusual Amino Acid |
|---|---|
| Adm | Adamantyl alanine |
| Ahp | 7-Amino heptanoic acid |
| Ana | 9-Anthracene alanine |
| Apa | 5-Amino pentanoic acid |
| Bip | (Paraphenyl)phenylalanine |
| Dip | 3,3-Diphenylalanine** |
| 3Hyp | 3-Hydroxyproline |
| 4Hyp | 4-Hydroxyproline |
| N-MeAsp | N-Methyl-Aspartic acid |
| N-MeDip | N-Methyl-3,3-Diphenylalanine |
| N-MeIle | N-Methyl-Isoleucine |
| N-MeLeu | N-Methyl-Leucine |
| N-MePhe | N-Methyl-Phenylalanine |
| N-MeTrp | N-Methyl-Tryptophan |
| Nva | Norvaline |
| Nle | Norleucine |
| Orn | Ornithine |
| Abu | 2-Aminobutyric acid |
| Alg | 2-Amino-4-pentenoic acid (Allylglycine) |
| Arg(NO$_2$) | N$^G$-nitroarginine |
| Atm | 2-Amino-3-(2-amino-5-thiazole)propanoic acid |
| Cpn | 2-Amino-3-cyclopropanepropanoic acid (Cyclopropylalanine) |
| Chex | Cyclohexylalanine (Hexahydrophenyl-alanine) |
| Dopa | 3,4-Dihydroxyphenylalanine |
| Emg | 2-Amino-4,5(RS)-epoxy-4-pentenoic acid |
| His(Dnp) | N$^{im}$-2,4-Dinitrophenylhistidine |
| HomoArg | Homoarginine |
| HomoGlu | 2-Aminoadipic acid |
| HomoPhe | 2-Amino-5-phenylpentanoic acid (Homophenylalanine) |
| HomoLys | 2,7-Diamino-Heptanoic acid (Homolysine) |
| Met(O) | Methionine sulfoxide |
| Met(O$_2$) | Methionine sulfone |
| 1-Nal | 3-(1'-Naphthyl)alanine |
| 2-Nal | 3-(2'-Naphthyl)alanine |
| Nia | 2-Amino-3-cyanopropanoic acid (Cyanoalanine) |
| Pgl | Phenylglycine |
| Pgy | 2-Aminopentanoic acid (Propylglycine) |
| Pha | 2-Amino-6-(1-pyrrolo)-hexanoic acid |
| Pmp | Pentamethylphenylalanine |
| Pyr | 2-Amino-3-(3-pyridyl)-propanoic acid (3-Pyridylalanine) |
| Tic | 1,2,3,4-Tetrahydro-3-isoquinolinecarboxylic acid |
| Tza | 2-Amino-3-(4-thiazolyl)-propanoic acid |
| Tyr(Ot-Bu) | O-tertiary butyl-tyrosine |

TABLE-continued

| | |
|---|---|
| Tyr(OMe) | O-Methyl-tyrosine |
| Tyr(OEt) | O-Ethyl-tyrosine |
| Trp(For) | N$^{in}$-Formyltryptophan |
| Trp-NH$_2$ | Tryptophan carboxamide |

| Abbreviation | Protecting Group |
|---|---|
| Ac | Acetyl |
| Ada | 1-Adamantyl acetic acid |
| Adoc | Adamantyloxycarbonyl |
| Bppa | 2,2-Diphenylpropionyl |
| Bz | Benzylcarbonyl |
| Bzl | Benzyl |
| CF$_3$CO | Trifluoroacetyl |
| Cxl | Cyclohexylacetyl |
| Cxl(U) | Cyclohexylurea |
| Et | Propionyl |
| Pya | 3-Pyridylacetal |
| MeBzl | 4-Methylbenzyl |
| Me(U) | Methylurea |
| Z | Benzyloxycarbonyl |
| 2-Br-Z | ortho-Bromobenzyloxycarbonyl |
| 2-Cl-Z | ortho-Chlorobenzyloxycarbonyl |
| Bom | Benzyloxymethyl |
| Boc | tertiary Butyloxycarbonyl |
| tBu | t-Butylcarbonyl |
| TBS | tertiary Butyldimethylsilyl |
| Dnp | 2,4-Dinitrophenyl |
| For | Formyl |
| Fmoc | 9-FLuoroenylmethyloxycarbonyl |
| NO$_2$ | Nitro |
| Tos | 4-Toluenesulfonyl (tosyl) |
| Trt | Triphenylmethyl (trityl) |

| Abbreviation | Solvents and Reagents |
|---|---|
| HOAc | Acetic acid |
| CH$_3$CN | Acetonitrile |
| DCM | Dichloromethane |
| DCC | N,N'-Dicyclohexylcarbodiimide |
| DIEA | N,N-Diisopropylethylamine |
| DMF | Dimethylformamide |
| HCl | Hydrochloric acid |
| HF | Hydrofluoric acid |
| HOBt | 1-Hydroxybenzotriazole |
| KOH | POtassium hydroxide |
| TFA | Trifluoroacetic acid |
| MBHA Resin | Methylbenzhydrylamine resin |
| PAM Resin | 4-(Oxymethyl)-phenylacetamidomethyl resin |

*If the optical activity of the amino acid is other than L(S), the amino acid or abbreviation is preceded by the appropriate configuration D(R) or DL(RS).
**Synthesis can be accomplished according to the procedure described by Josien, H., et al, Tetrahedron Letters, 1991, 32, 6547–50.

The compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S. M., et al, "Pharmaceutical Salts," *Journal of Pharmaceutical Science*, 66, pp. 1–19 (1977)).

The acid addition salts of said basic compounds are prepared by contacting the free base form with a sufficient amount of the desired acid to produce the salt in the conventional manner. Preferably a peptide of Formula I can be converted to an acidic salt by treating with an aqueous solution of the desired base, such that the resulting pH is less than 4. The solution can be passed through a C18 cartridge to absorb the peptide, washed with copious amounts of water, the peptide eluted with a polar organic solvent such as, for example, methanol, acetonitrile, and the like, and isolated by concentrating under reduced pressure followed by lyophilization. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge, S. M., et al, "Pharmaceutical Salts," *Journal of Pharmaceutical Science*, 66, pp. 1–19 (1977)).

The base addition salts of said acidic compounds are prepared by contacting the free acid form with a sufficient amount of the desired base to produce the salt in the conventional manner. Preferably, a peptide of Formula I can be converted to a base salt by treating with an aqueous solution of the desired base, such that the resulting pH is greater than 9. The solution can be passed through a C18 cartridge to absorb the peptide, washed with copious amounts of water, the peptide eluted with a polar organic solvent such as, for example, methanol, acetonitrile and the like, and isolated by concentrating under reduced pressure followed by lyophilization. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

A preferred compound of Formula I is one wherein AA¹ is

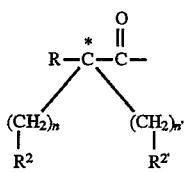

wherein R is hydrogen alkyl, alkenyl, alkynyl, cycloalkyl, cycloalkylalkyl, aryl, heteroaryl, fluorenylmethyl,

wherein $R^3$ and $R^4$ are each the same or different and each is hydrogen, alkyl, alkenyl, alkynyl, cycloalkyl, cycloalkylalkyl, aryl, heteroaryl, or fluorenylmethyl,

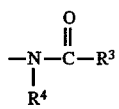

wherein $R^3$ and $R^4$ are each the same or different and each is as defined above or

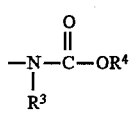

wherein and are each the same or different and each is as defined above,

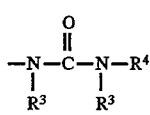

wherein $R^3$ and $R^4$ are defined above, or

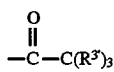

wherein $R^{3'}$ is F, Cl, Br, or I, n is zero, $R^2$ is hydrogen or methyl, n' is zero or an integer of 1, 2, or 3, and $R^{2'}$ is hydrogen, trityl, aryl, heteroaryl, heterocycloalkyl,

wherein $R^3$ and $R^4$ are each the same or different and each is as defined above or

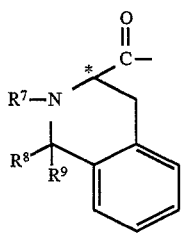

wherein $R^7$ is hydrogen, alkyl, aryl, or heteroaryl, $R^8$ and $R^9$ are each the same or different and each is hydrogen or alkyl,

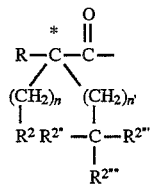

wherein $R^{2''}$, $R^{2'''}$, and $R^{2''''}$ are each the same or different and each is hydrogen, alkyl, aryl, or heteroaryl with the proviso that at least one of $R^{2''}$, $R^{2'''}$, and $R^{2''''}$ is aryl or heteroaryl and $R^2$, n, and n' are as defined above, or

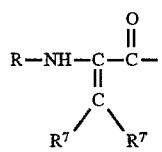

wherein $R^7$ and $R^{7'}$ are each the same or different and each is hydrogen, alkyl, cycloalkyl, aryl, or heteroaryl;

$AA^2$, $AA^3$, $AA^4$, and $AA^5$ are each independently absent or each independently; Ahp, Dip, Apa, Pro, Phe, or

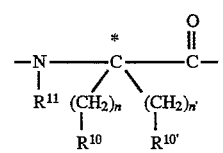

wherein
$R^{11}$ is hydrogen or methyl,
n is zero,
$R^{10}$ is hydrogen or methyl,
n' is zero or an integer of 1, 2, 3, or 4 and
$R^{10'}$ is hydrogen, alkyl, cycloalkyl, alkenyl, alkynyl, —$OR^{3''}$ wherein $R^{3''}$ is hydrogen, alkyl, alkenyl, cycloalkyl, aryl, or heteroaryl,

wherein $R^{3''}$ and $R^{4'}$ are each the same or different and each is as defined above for $R^{3''}$,

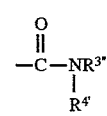

wherein $R^{3''}$ and $R^{4'}$ are each the same or different and each is as defined above for $R^{3''}$,

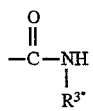

wherein $R^{3''}$ is as defined above,

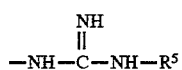

wherein $R^5$ is defined as above,

wherein $R^{3''}$ is as defined above —$S(O)_mR^{3''}$ wherein m is zero or an integer of 1 of 2 and $R^{3''}$ is as defined above except that $R^{3''}$ is not hydrogen, or

wherein $R^{4'}$ is as defined above, $AA^6$ is

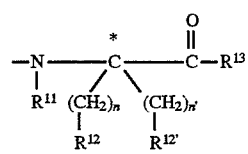

wherein $R^{11}$ is hydrogen or methyl, n is zero, $R^{12}$ is hydrogen, or methyl, n' is zero or an integer of 1, 2, or 3, $R^{12'}$ is aryl or heteroaryl, $R^{13}$ is —$(CH_2)_n$—$CO_2H$ wherein n is as defined above, —$(CH_2)_n$—OH wherein n is as defined above, or

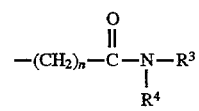

wherein n, $R^3$, and $R^4$ are defined above, $$-\overset{\overset{\displaystyle O}{\|}}{C}-NH-\underset{\underset{\displaystyle R^{14}}{|}}{CH}-CO_2H$$

wherein $R^{14}$ is hydrogen or —$CH_2$—$CO_2H$, or

[structure: tetrahydro-β-carboline-type ring system with substituents $R^{13}$, $R^8$, $R^9$, $R^{8'}$ and N positions marked with *]

wherein $R^8$ and $R^9$ are each the same or different and each is as defined above for and $R^9$ and $R^{13}$ is as defined above, and $R^{8'}$ is hydrogen, formyl, acetyl, Z, Boc, Bzl, or alkyl;

stereochemistry at $\overset{*}{c}$ in $AA^1$ is D, stereochemistry at $\overset{*}{c}$ in $AA^2$, $AA^3$, $AA^4$, or $AA^5$ is D, L, or DL, and stereochemistry at $\overset{*}{c}$ in $AA^6$ is L.

Most preferred compounds of Formula I are one wherein $AA^1$ is

[structure: R—C(*)—C(=O)— with branches (CH$_2$)$_n$—R$^2$ and (CH$_2$)$_{n'}$—C(R$^{2'}$)(R$^{2''}$)—R$^{2'''}$]

wherein R is hydrogen, alkyl, alkenyl, alkynyl, cycloalkyl, cycloalkylalkyl, aryl, heteroaryl, fluorenylmethyl, $$-\underset{\underset{\displaystyle R^4}{|}}{N}-R^3$$

wherein $R^3$ and $R^4$ are each the same or different and each is hydrogen, alkyl, alkenyl, alkynyl, cycloalkyl, cycloalkylalkyl, aryl, heteroaryl, or fluorenylmethyl, $$-\underset{\underset{\displaystyle R^3}{|}}{N}-\overset{\overset{\displaystyle O}{\|}}{C}-R^4$$

wherein $R^3$ and $R^4$ are each the same or different and is as defined above, $$-\underset{\underset{\displaystyle R^4}{|}}{N}-\overset{\overset{\displaystyle O}{\|}}{C}-OR^4$$

wherein $R^3$ and $R^4$ are each the same or different and each is as defined above, and $R^{2'}$, $R^{2''}$, and $R^{2'''}$ are each the same or different and each is hydrogen, alkyl, aryl, or heteroaryl with the proviso that at least one of $R^2$, $R^{2'}$, and $R^{2''}$ is aryl or heteroaryl, and $R^{2'''}$ is hydrogen or methyl, $$-\underset{\underset{\displaystyle R^3}{|}}{N}-\overset{\overset{\displaystyle O}{\|}}{C}-\underset{\underset{\displaystyle R^3}{|}}{N}-R^4$$

wherein $R^3$ and $R^4$ are defined above, or $$-\overset{\overset{\displaystyle O}{\|}}{C}-C(R^{3'})_3$$

wherein $R^{3'}$ is F, Cl, Br, or I,
$R^2$ is hydrogen or methyl,
n is zero, and
n' is zero or an integer of 1, 2, or 3, or
$AA^2$ is Apa, Aha, Dip, D-Phe, Phe, HomoArg, Arg, or

[structure: —N(R$^{11}$)—C(*)—C(=O)— with branches (CH$_2$)$_n$—R$^{10}$ and (CH$_2$)$_{n'}$—R$^{10'}$]

wherein
$R^{11}$ is hydrogen or methyl,
n is zero,
$R^{10}$ is hydrogen or methyl,
n' is zero or an integer of 1, 2, 3, 4, or 5, and
$R^{10}$ is alkyl, OH, $$-\underset{\underset{\displaystyle R^{4'}}{|}}{N}-R^{3''}$$

wherein $R^{3''}$ and $R^{4'}$ are each the same or different and each is hydrogen, alkyl, or aryl, $$-\overset{\overset{\displaystyle O}{\|}}{C}-\underset{\underset{\displaystyle R^{4'}}{|}}{N}-R^{3''}$$

wherein $R^{3''}$ and $R^{4'}$ are as defined above, $$-\overset{\overset{\displaystyle O}{\|}}{C}-OR^{4'}$$

wherein $R^{4'}$ is as defined above; —$S(O)_m R^{3''}$ wherein m is zero or an integer of 1 of 2 and $R^{3''}$ is as defined above except that $R^{3''}$ is not hydrogen;

$AA^3$ is Lys, Tyr, Phe, or

[structure: —N(R$^{11}$)—C(*)—C(=O)— with branches (CH$_2$)$_n$—R$^{10}$ and (CH$_2$)$_{n'}$—R$^{10'}$]

wherein
$R^{11}$ is hydrogen or methyl,
n is zero,
$R^{10}$ is hydrogen or methyl, n" is zero or an integer of 1, 2, or 3, and
$R^{11'}$ is alkyl, aryl,

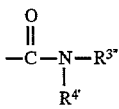

wherein $R^{3''}$ and $R^{4'}$ are as defined above,

wherein $R^{4'}$ is as defined above,
$AA^4$ and $AA^5$ are each Phe, Lys, Glu, Pro, or

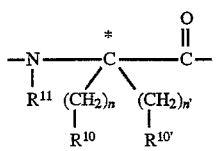

wherein
$R^{11}$ is hydrogen or methyl,
n is zero,
$R^{10}$ is hydrogen or methyl,
n' is zero, and
$R^{10'}$ is alkyl, or cycloalkyl,
$AA^6$ is

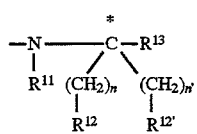

wherein
$R^{11}$ is hydrogen or methyl,
n is zero,
$R^{12}$ is hydrogen, or methyl,
n' is zero or an integer of 1, 2, of 3,
$R^{12'}$ is aryl or heteroaryl,
$R^{13}$ is —$(CH_2)_n$—$CO_2H$ wherein n is zero or an integer of 1, 2, 3, 4, 5, or 6, —$(CH_2)_n$—OH wherein n is zero or an integer of 1, 2, 3, 4, 5, or 6, or

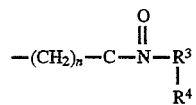

wherein n, $R^3$, and $R^4$ are defined above,

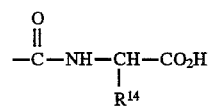

wherein $R^{14}$ is hydrogen or —$CH_2CO_2H$,
stereochemistry at * c in $AA^1$ is D,
stereochemistry at * c in $AA^2$, $AA^3$, $AA^4$, or $AA^5$ is D or L and
stereochemistry at * c in $AA^6$ is L.
A more preferred compound of Formula I is one wherein $AA^1$ is D-Adm,
D-Ana,
D-Chx,
D-Dip,
D-Dopa,
D-Bip,
D-His,
D-His (Dnp),
D-2-Nal,
D-1-Nal,
D-Phe,
D-Pmp,
D-Pgl,
D-Tyr,
D-Tyr(OMe),
D-Tyr(OEt),
D-Tyr(OtBu),
D-Trp,
D-Trp(For),
D-Tic,
D-Tza,
D-Pyr,
Ac-D-Adm,
Ac-D-Ana,
Ac-D-Chx,
Ac-D-Dip,
Ac-D-Dopa,
Ac-D-Bip,
Ac-D-His,
Ac-D-His(Dnp),
Ac-D-2-Nal,
Ac-D-1-Nal,
Ac -D-N-MeDip,
Ac-D-Phe,
Ac-D-Pgl,
Ac-D-Pmp,
Ac-D-Tyr,
Ac-D-Tyr(OMe),
Ac-D-Tyr(OEt),
Ac-D-Tyr(OtBu),
Ac-D-Trp,
Ac-D-Trp(For),
Ac-D-Tic,
Ac-D-Tza,
Ac-D-Pyr,
Ada-D-Adm,
Ada-D-Ana,
Ada-D-Chx,
Ada-D-Dip,
Ada-D-Dopa,
Ada-D-Bip,
Ada-D-His,
Ada-D-His(Dnp),
Ada-D-2-Nal,
Ada-D-1-Nal,
Ada-D-Pmp,
Ada-D-Phe,
Ada-D-Pgl,
Ada-D-Tyr,
Ada-D-Tyr(OMe),
Ada-D-Tyr(OEt),
Ada-D-Tyr(OtBu),
Ada-D-Trp,
Ada-D-Trp(For),
Ada-D-Tic,
Ada-D-Tza,
Ada-D-Pyr,
Adoc-D-Adm, Adoc-D-Ana,
Adoc-D-Chx,
Adoc-D-Dip,
Adoc-D-Dopa,
Adoc-D-Bip,
Adoc-D-His,
Adoc-D-His(Dnp),
Adoc-D-2-Nal,
Adoc-D-1-Nal,
Adoc-D-Phe,
Adoc-D-Pmp,
Adoc-D-Pgl,
Adoc-D-Tyr,
Adoc-D-Tyr(OMe),
Adoc-D-Tyr(OEt),
Adoc-D-Tyr(OtBu),
Adoc-D-Trp,
Adoc-D-Trp(For),
Adoc-D-Tic,
Adoc-D-Tza,
Adoc-D-Pyr,
Boc-D-Adm,
Boc-D-Ana,
Boc-D-Chx,
Boc-D-Dip,
Boc-D-Dopa,
Boc-D-Bip,
Boc-D-His,
Boc-D-His(Dnp),
Boc-D-2-Nal,
Boc-D-1-Nal,
Boc-D-Phe,
Boc-D-Pmp,
Boc-D-Pgl,
Boc-D-Tyr,
Boc-D-Tyr(OMe),
Boc-D-Tyr(OEt),
Boc-D-Tyr(OtBu),
Boc-D-Trp,
Boc-D-Trp(For),
Boc-D-Tic,
Boc-D-Tza,
Boc-D-Pyr,
Z-D-Adm,
Z-D-Ana,
Z-D-Chx,
Z-D-Dip,
Z-D-Dopa,
Z-D-Bip,
Z-D-His,
Z-D-His(Dnp),
Z-D-2-Nal,
Z-D-1-Nal,
Z-D-Phe,
Z-D-Pmp,
Z-D-Pgl,
Z-D-Tyr,
Z-D-Tyr(OMe),
Z-D-Tyr(OEt),
Z-D-Tyr(OtBu),
Z-D-Trp,
Z-D-Trp(For),
Z-D-Tic,
Z-D-Tza,
Z-D-Pyr,
Fmoc-D-Adm,
Fmoc-D-Ana,
Fmoc-D-Chx,
Fmoc-D-Dip,
Fmoc-D-Dopa,
Fmoc-D-Bip,
Fmoc-D-His,
Fmoc-D-His(Dnp),
Fmoc-D-2-Nal,
Fmoc-D-1-Nal,
Fmoc-D-Phe,
Fmoc-D-Pmp,
Fmoc-D-Pgl,
Fmoc-D-Tyr,
Fmoc-D-Tyr(OMe),
Fmoc-D-Tyr(OEt),
Fmoc-D-Tyr(OtBu),
Fmoc-D-Trp,
Fmoc-D-Trp(For),
Fmoc-D-Tic,
Fmoc-D-Tza,
Fmoc-D-Pyr,
Et-D-Dip,
Bz-D-Dip,
Pya-D-Dip,
Cxl-D-Dip,
Ada-D-Dip,
Cxl(U)-D-Dip,
Me(U)-D-Dip,
tBu-D-Dip,
$CF_3CO$-D-Dip;
$AA^2$ is
Ala,
Alg,
Aha,
Apa,
Arg,
Asn,
Asp,
Dab,
D-Dip,
Glu,
Gln,
Gly,
HomoArg,
HomoGlu,
HomoLys,
Ile,
Leu,
D-Leu,
Lys,
D-N-MeLeu,
Met,
Met(O),
Met($O_2$),
Nva,
Nle,
Orn,
Phe,
D-Phe,
Tyr,
Val, or
$AA^2$ is absent;
$AA^3$ is
Asn,
Asp,
D-Asp,
N-MeAsp,
Glu, Gln,
Lys,
HomoPhe,
Phe,
Tyr, or
AA³ is absent;
AA⁴ is
Ala,
Chx,
Gly,
Glu,
Ile,
D-Ile,
Leu,
Lys,
Nle,
N-MeIle,
Nva,
Phe,
Pro,
Val, or
AA⁴ is absent;
AA⁵ is Ala,
Chx,
Gly,
Ile,
D-Ile,
Leu,
Lys,
Nle,
N-MeIle,
Nva,
Phe,
Val, or
AA⁵ is absent; and
AA⁶ is
2-Nal,
1-Nal,
N-MeTrp,
Phe,
Pyr,
Trp,
Trp-NH₂,
Tyr(OMe),
Tyr(OEt),
Tyr(Ot-Bu),
Tyr,
Trp-Gly,
Trp-Asp,
Trp(For),
Dip,
Phe, or

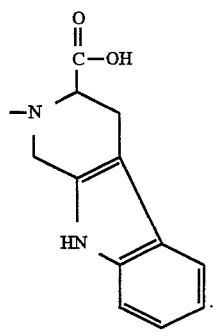

Particularly valuable are:

D-Phe-Leu-Asp-Ile-Ile-Trp;
D-His(Dnp)-Leu-Asp-Ile-Ile-Trp;
D-Trp-Leu-Asp-Ile-Ile-Trp;
D-Tyr-Leu-Asp-Ile-Ile-Trp;
D-Tyr(OMe)-Leu-Asp-Ile-Ile-Trp;
D-Tyr(OEt)-Leu-Asp-Ile-Ile-Trp;
D-2-Nal-Leu-Asp-Ile-Ile-Trp;
D-1-Nal-Leu-Asp-Ile-Ile-Trp;
D-Pgl-Leu-Asp-Ile-Ile-Trp;
D-Pyr-Leu-Asp-Ile-Ile-Trp;
D-Tic-Leu-Asp-Ile-Ile-Trp;
D-Dip-Leu-Asp-Ile-Ile-Trp;
D-Bip-Leu-Asp-Ile-Ile-Trp;
Ac-D-Phe-Leu-Asp-Ile-Ile-Trp;
Ac-D-His(Dnp)-Leu-Asp-Ile-Ile-Trp;
Ac-D-Trp-Leu-Asp-Ile-Ile-Trp;
Ac-D-Tyr-Leu-Asp-Ile-Ile-Trp;
Ac-D-Tyr(OMe)-Leu-Asp-Ile-Ile-Trp;
Ac-D-Tyr(OEt)-Leu-Asp-Ile-Ile-Trp;
Ac-D-2-Nal-Leu-Asp-Ile-Ile-Trp;
Ac-D-1-Nal-Leu-Asp-Ile-Ile-Trp;
Ac-D-Pgl-Leu-Asp-Ile-Ile-Trp;
Ac-D-Pyr-Leu-Asp-Ile-Ile-Trp;
Ac-D-Tic-Leu-Asp-Ile-Ile-Trp;
Ac-D-Dip-Leu-Asp-Ile-Ile-Trp;
Ac-D-Bip-Leu-Asp-Ile-Ile-Trp;
Fmoc-D-Phe-Leu-Asp-Ile-Ile-Trp;
Fmoc-D-His-Leu-Asp-Ile-Ile-Trp;
Fmoc-D-Trp-Leu-Asp-Ile-Ile-Trp;
Fmoc-D-Tyr-Leu-Asp-Ile-Ile-Trp;
Fmoc-D-Tyr(OMe)-Leu-Asp-Ile-Ile-Trp;
Fmoc-D-Tyr(OEt)-Leu-Asp-Ile-Ile-Trp;
Fmoc-D-2-Nal-Leu-Asp-Ile-Ile-Trp;
Fmoc-D-1-Nal-Leu-Asp-Ile-Ile-Trp;
Fmoc-D-Dip-Leu-Asp-Ile-Ile-Trp;
Fmoc-D-Bip-Leu-Asp-Ile-Ile-Trp;
Ada-D-Phe-Leu-Asp-Ile-Ile-Trp;
Ada-D-His-Leu-Asp-Ile-Ile-Trp;
Ada-D-Trp-Leu-Asp-Ile-Ile-Trp;
Ada-D-Tyr-Leu-Asp-Ile-Ile-Trp;
Ada-D-Tyr(OMe)-Leu-Asp-Ile-Ile-Trp;
Ada-D-Tyr(OEt)-Leu-Asp-Ile-Ile-Trp;
Ada-D-2-Nal-Leu-Asp-Ile-Ile-Trp;
Ada-D-1-Nal-Leu-Asp-Ile-Ile-Trp;
Ada-D-Dip-Leu-Asp-Ile-Ile-Trp;
Ada-D-Bip-Leu-Asp-Ile-Ile-Trp;
Ac-D-Phe-D-Leu-Asp-Ile-Ile-Trp;
Ac-D-His-D-Leu-Asp-Ile-Ile-Trp;
Ac-D-Trp-D-Leu-Asp-Ile-Ile-Trp;
Ac-D-Tyr-D-Leu-Asp-Ile-Ile-Trp;
Ac-D-Tyr(OMe)-D-Leu-Asp-Ile-Ile-Trp;
Ac-D-Tyr(OEt)-D-Leu-Asp-Ile-Ile-Trp;
Ac-D-2-Nal-D-Leu-Asp-Ile-Ile-Trp;
Ac-D-1-Nal-D-Leu-Asp-Ile-Ile-Trp;
Ac-D-Dip-D-Leu-Asp-Ile-Ile-Trp;
Ac-D-Bip-D-Leu-Asp-Ile-Ile-Trp;
Ac-D-Phe-Ile-Asp-Ile-Ile-Trp;
Ac-D-His-Ile-Asp-Ile-Ile-Trp;
Ac-D-Trp-Ile-Asp-Ile-Ile-Trp;
Ac-D-Tyr-Ile-Asp-Ile-Ile-Trp;
Ac-D-Tyr(OMe)-Ile-Asp-Ile-Ile-Trp;
Ac-D-Tyr(OEt)-Ile-Asp-Ile-Ile-Trp;
Ac-D-2-Nal-Ile-Asp-Ile-Ile-Trp;
Ac-D-1-Nal-Ile-Asp-Ile-Ile-Trp;
Ac-D-Dip-Ile-Asp-Ile-Ile-Trp;
Ac-D-Bip-Ile-Asp-Ile-Ile-Trp;
Ac-D-Phe-Val-Asp-Ile-Ile-Trp;
Ac-D-His-Val-Asp-Ile-Ile-Trp;

Ac-D-Trp-Val-Asp-Ile-Ile-Trp;
Ac-D-Tyr-Val-Asp-Ile-Ile-Trp;
Ac-D-Tyr(OMe)-Val-Asp-Ile-Ile-Trp;
Ac-D-Tyr(OEt)-Val-Asp-Ile-Ile-Trp;
Ac-D-2-Nal-Val-Asp-Ile-Ile-Trp;
Ac-D-1-Nal-Val-Asp-Ile-Ile-Trp;
Ac-D-Dip-Val-Asp-Ile-Ile-Trp;
Ac-D-Bip-Val-Asp-Ile-Ile-Trp;
Ac-D-Phe-Dab-Asp-Ile-Ile-Trp;
Ac-D-His-Dab-Asp-Ile-Ile-Trp;
Ac-D-Trp-Dab-Asp-Ile-Ile-Trp;
Ac-D-Tyr(OMe)-Dab-Asp-Ile-Ile-Trp;
Ac-D-Tyr(OEt)-Dab-Asp-Ile-Ile-Trp;
Ac-D-2-Nal-Dab-Asp-Ile-Ile-Trp;
Ac-D-1-Nal-Dab-Asp-Ile-Ile-Trp;
Ac-D-Dip-Dab-Asp-Ile-Ile-Trp;
Ac-D-Bip-Dab-Asp-Ile-Ile-Trp;
Ac-D-Phe-Arg-Asp-Ile-Ile-Trp;
Ac-D-His-Arg-Asp-Ile-Ile-Trp;
Ac-D-Trp-Arg-Asp-Ile-Ile-Trp;
Ac-D-Tyr(OMe)-Arg-Asp-Ile-Ile-Trp;
Ac-D-Tyr(OEt)-Arg-Asp-Ile-Ile-Trp;
Ac-D-2-Nal-Arg-Asp-Ile-Ile-Trp;
Ac-D-1-Nal-Arg-Asp-Ile-Ile-Trp;
Ac-D-Dip-Arg-Asp-Ile-Ile-Trp;
Ac-D-Bip-Arg-Asp-Ile-Ile-Trp;
Ac-D-Phe-HomoLys-Asp-Ile-Ile-Trp;
Ac-D-His-HomoLys-Asp-Ile-Ile-Trp;
Ac-D-Trp-HomoLys-Asp-Ile-Ile-Trp;
Ac-D-Tyr(OMe)-HomoLys-Asp-Ile-Ile-Trp;
Ac-D-Tyr(OEt)-HomoLys-Asp-Ile-Ile-Trp;
Ac-D-2-Nal-HomoLys-Asp-Ile-Ile-Trp;
Ac-D-1-Nal-HomoLys-Asp-Ile-Ile-Trp;
Ac-D-Dip-HomoLys-Asp-Ile-Ile-Trp;
Ac-D-Bip-HomoLys-Asp-Ile-Ile-Trp;
Ac-D-His-Glu-Asp-Ile-Ile-Trp;
Ac-D-Trp-Glu-Asp-Ile-Ile-Trp;
Ac-D-Tyr(OMe)-Glu-Asp-Ile-Ile-Trp;
Ac-D-Tyr(OEt)-Glu-Asp-Ile-Ile-Trp;
Ac-D-2-Nal-Glu-Asp-Ile-Ile-Trp;
Ac-D-1-Nal-Glu-Asp-Ile-Ile-Trp;
Ac-D-Dip-Glu-Asp-Ile-Ile-Trp;
Ac-D-Bip-Glu-Asp-Ile-Ile-Trp;
Ac-D-Phe-HomoGlu-Asp-Ile-Ile-Trp;
Ac-D-His-HomoGlu-Asp-Ile-Ile-Trp;
Ac Trp-HomoGlu-Asp-Ile-Ile-Trp;
Ac-D-Tyr(OMe)-HomoGlu-Asp-Ile-Ile-Trp;
Ac-D-Tyr(OEt)-HomoGlu-Asp-Ile-Ile-Trp;
Ac-D-2-Nal-HomoGlu-Asp-Ile-Ile-Trp;
Ac-D-1-Nal-HomoGlu-Asp-Ile-Ile-Trp;
Ac-D-Dip-HomoGlu-Asp-Ile-Ile-Trp;
Ac-D-Bip-HomoGlu-Asp-Ile-Ile-Trp;
Ac-D-Phe-Asp-Asp-Ile-Ile-Trp;
Ac-D-His-Asp-Asp-Ile-Ile-Trp;
Ac Trp-Asp-Asp-Ile-Ile-Trp;
Ac-D-Tyr(OMe)-Asp-Asp-Ile-Ile-Trp;
Ac-D-Tyr(OEt)-Asp-Asp-Ile-Ile-Trp;
Ac-D-2-Nal-Asp-Asp-Ile-Ile-Trp;
Ac-D-1-Nal-Asp-Asp-Ile-Ile-Trp;
Ac-D-Dip-Asp-Asp-Ile-Ile-Trp;
Ac-D-Bip-Asp-Asp-Ile-Ile-Trp;
Ac-D-Phe-Lys-Asp-Ile-Ile-Trp;
Ac-D-His-Lys-Asp-Ile-Ile-Trp;
Ac-D-Trp-Lys-Asp-Ile-Ile-Trp;
Ac-D-Tyr-Lys-Asp-Ile-Ile-Trp;
Ac-D-Tyr(OMe)-Lys-Asp-Ile-Ile-Trp;
Ac-D-Tyr(OEt)-Lys-Asp-Ile-Ile-Trp;
Ac-D-2-Nal-Lys-Asp-Ile-Ile-Trp;
Ac-D-1-Nal-Lys-Asp-Ile-Ile-Trp;
Ac-D-Dip-Lys-Asp-Ile-Ile-Trp;
Ac-D-Bip-Lys-Asp-Ile-Ile-Trp;
Ac-D-Phe-Orn-Asp-Ile-Ile-Trp;
Ac-D-His-Orn-Asp-Ile-Ile-Trp;
Ac-D-Trp-Orn-Asp-Ile-Ile-Trp;
Ac-D-Tyr-Orn-Asp-Ile-Ile-Trp;
Ac-D-Tyr(OMe)-Orn-Asp-Ile-Ile-Trp;
Ac-D-Tyr(OEt)-Orn-Asp-Ile-Ile-Trp;
Ac-D-2-Nal-Orn-Asp-Ile-Ile-Trp;
Ac-D-1-Nal-Orn-Asp-Ile-Ile-Trp;
Ac-D-Dip-Orn-Asp-Ile-Ile-Trp;
Ac-D-Bip-Orn-Asp-Ile-Ile-Trp;
Ac-D-Phe-Gln-Asp-Ile-Ile-Trp;
Ac-D-His-Gln-Asp-Ile-Ile-Trp;
Ac-D-Trp-Gln-Asp-Ile-Ile-Trp;
Ac-D-Tyr-Gln-Asp-Ile-Ile-Trp;
Ac-D-Tyr(OMe)-Gln-Asp-Ile-Ile-Trp;
Ac-D-Tyr(OEt)-Gln-Asp-Ile-Ile-Trp;
Ac-D-2-Nal-Gln-Asp-Ile-Ile-Trp;
Ac-D-1-Nal-Gln-Asp-Ile-Ile-Trp;
Ac-D-Dip-Gln-Asp-Ile-Ile-Trp;
Ac-D-Bip-Gln-Asp-Ile-Ile-Trp;
Ac-D-Phe-Leu-Glu-Ile-Ile-Trp;
Ac-D-His-Leu-Glu-Ile-Ile-Trp;
Ac-D-Trp-Leu-Glu-Ile-Ile-Trp;
Ac-D-Tyr-Leu-Glu-Ile-Ile-Trp;
Ac-D-Tyr(OMe)-Leu-Glu-Ile-Ile-Trp;
Ac-D-Tyr(OEt)-Leu-Glu-Ile-Ile-Trp;
Ac-D-2-Nal-Leu-Glu-Ile-Ile-Trp;
Ac-D-1-Nal-Leu-Glu-Ile-Ile-Trp;
Ac-D-Dip-Leu-Glu-Ile-Ile-Trp;
Ac-D-Bip-Leu-Glu-Ile-Ile-Trp;
Ac-D-Phe-Leu-Asn-Ile-Ile-Trp;
Ac-D-His-Leu-Asn-Ile-Ile-Trp;
Ac-D-Trp-Leu-Asn-Ile-Ile-Trp;
Ac-D-Tyr-Leu-Asn-Ile-Ile-Trp;
Ac-D-Tyr(OMe)-Leu-Asn-Ile-Ile-Trp;
Ac-D-Tyr(OEt)-Leu-Asn-Ile-Ile-Trp;
Ac-D-2-Nal-Leu-Asn-Ile-Ile-Trp;
Ac-D-1-Nal-Leu-Asn-Ile-Ile-Trp;
Ac-D-Dip-Leu-Asn-Ile-Ile-Trp;
Ac-D-Bip-Leu-Asn-Ile-Ile-Trp;
Ac-D-Phe-Leu-Phe-Ile-Ile-Trp;
Ac-D-His-Leu-Phe-Ile-Ile-Trp;
Ac-D-Trp-Leu-Phe-Ile-Ile-Trp;
Ac-D-Tyr(OMe)-Leu-Phe-Ile-Ile-Trp;
Ac-D-Tyr(OEt)-Leu-Phe-Ile-Ile-Trp;
Ac-D-2-Nal-Leu-Phe-Ile-Ile-Trp;
Ac-D-1-Nal-Leu-Phe-Ile-Ile-Trp;
Ac-D-Dip-Leu-Phe-Ile-Ile-Trp;
Ac-D-Bip-Leu-Phe-Ile-Ile-Trp;
Ac-D-Phe-Glu-Asp-Ile-Ile-Trp;
Ac-D-Phe-Leu-Asp-Val-Ile-Trp;
Ac-D-His-Leu-Asp-Val-Ile-Trp;
Ac-D-Trp-Leu-Asp-Val-Ile-Trp;
Ac-D-Tyr-Leu-Asp-Val-Ile-Trp;
Ac-D-Tyr(OMe)-Leu-Asp-Val-Ile-Trp;
Ac-D-Tyr(OEt)-Leu-Asp-Val-Ile-Trp;
Ac-D-2-Nal-Leu-Asp-Val-Ile-Trp;
Ac-D-1-Nal-Leu-Asp-Val-Ile-Trp;
Ac-D-Dip-Leu-Asp-Val-Ile-Trp;
Ac-D-Bip-Leu-Asp-Val-Ile-Trp;
Ac-D-Phe-Leu-Asp-Chx-Ile-Trp;
Ac-D-His-Leu-Asp-Chx-Ile-Trp;
Ac-D-Trp-Leu-Asp-Chx-Ile-Trp;

Ac-D-Tyr-Leu-Asp-Chx-Ile-Trp;
Ac-D-Tyr(OMe)-Leu-Asp-Chx-Ile-Trp;
Ac-D-Tyr(OEt)-Leu-Asp-Chx-Ile-Trp;
Ac-D-2-Nal-Leu-Asp-Chx-Ile-Trp;
Ac-D-1-Nal-Leu-Asp-Chx-Ile-Trp;
Ac-D-Dip-Leu-Asp-Chx-Ile-Trp;
Ac-D-Bip-Leu-Asp-Chx-Ile-Trp;
Ac-D-Phe-Leu-Asp-D-Ile-Ile-Trp;
Ac-D-His-Leu-Asp-D-Ile-Ile-Trp;
Ac-D-Trp-Leu-Asp-D-Ile-Ile-Trp;
Ac-D-Tyr-Leu-Asp-D-Ile-Ile-Trp;
Ac-D-Tyr(OMe)-Leu-Asp-D-Ile-Ile-Trp;
Ac-D-Tyr(OEt)-Leu-Asp-D-Ile-Ile-Trp;
Ac-D-2-Nal-Leu-Asp-D-Ile-Ile-Trp;
Ac-D-1-Nal-Leu-Asp-D-Ile-Ile-Trp;
Ac-D-Dip-Leu-Asp-D-Ile-Ile-Trp;
Ac-D-Bip-Leu-Asp-D-Ile-Ile-Trp;
Ac-D-Phe-Leu-Asp-Ile-D-Ile-Trp;
Ac-D-His-Leu-Asp-Ile-D-Ile-Trp;
Ac-D-Trp-Leu-Asp-Ile-D-Ile-Trp;
Ac-D-Tyr-Leu-Asp-Ile-D-Ile-Trp;
Ac-D-Tyr(OMe)-Leu-Asp-Ile-D-Ile-Trp;
Ac-D-Tyr(OEt)-Leu-Asp-Ile-D-Ile-Trp;
Ac-D-2-Nal-Leu-Asp-Ile-D-Ile-Trp;
Ac-D-1-Nal-Leu-Asp-Ile-D-Ile-Trp;
Ac-D-Dip-Leu-Asp-Ile-D-Ile-Trp;
Ac-D-Bip-Leu-Asp-Ile-D-Ile-Trp;
Ac-D-Phe-Leu-Asp-Ile-Val-Trp;
Ac-D-His-Leu-Asp-Ile-Val-Trp;
Ac-D-Trp-Leu-Asp-Ile-Val-Trp;
Ac-D-Tyr-Leu-Asp-Ile-Val-Trp;
Ac-D-Tyr(OMe)-Leu-Asp-Ile-Val-Trp;
Ac-D-Tyr(OEt)-Leu-Asp-Ile-Val-Trp;
Ac-D-2-Nal-Leu-Asp-Ile-Val-Trp;
Ac-D-1-Nal-Leu-Asp-Ile-Val-Trp;
Ac-D-Dip-Leu-Asp-Ile-Val-Trp;
Ac-D-Bip-Leu-Asp-Ile-Val-Trp;
Ac-D-Phe-Leu-Asp-Ile-Chx-Trp;
Ac-D-His-Leu-Asp-Ile-Chx-Trp;
Ac-D-Trp-Leu-Asp-Ile-Chx-Trp;
Ac-D-Tyr-Leu-Asp-Ile-Chx-Trp;
Ac-D-Tyr(OMe)-Leu-Asp-Ile-Chx-Trp;
Ac-D-Tyr(OEt)-Leu-Asp-Ile-Chx-Trp;
Ac-D-2-Nal-Leu-Asp-Ile-Chx-Trp;
Ac-D-1-Nal-Leu-Asp-Ile-Chx-Trp;
Ac-D-Dip-Leu-Asp-Ile-Chx-Trp;
Ac-D-Bip-Leu-Asp-Ile-Chx-Trp;
Ac-D-Phe-Leu-Asp-Ile-Ile-2-Nal;
Ac-D-His-Leu-Asp-Ile-Ile-2-Nal;
Ac-D-Trp-Leu-Asp-Ile-Ile-2-Nal;
Ac-D-Tyr-Leu-Asp-Ile-Ile-2-Nal;
Ac-D-Tyr(OMe)-Leu-Asp-Ile-Ile-2-Nal;
Ac-D-Tyr(OEt)-Leu-Asp-Ile-Ile-2-Nal;
Ac-D-2-Nal-Leu-Asp-Ile-Ile-2-Nal;
Ac-D-1-Nal-Leu-Asp-Ile-Ile-2-Nal;
Ac-D-Dip-Leu-Asp-Ile-Ile-2-Nal;
Ac-D-Bip-Leu-Asp-Ile-Ile-2-Nal;
Ac-D-Phe-Leu-Asp-Ile-Ile-1-Nal;
Ac-D-His-Leu-Asp-Ile-Ile-1-Nal;
Ac-D-Trp-Leu-Asp-Ile-Ile-1-Nal;
Ac-D-Tyr-Leu-Asp-Ile-Ile-1-Nal;
Ac-D-Tyr(OMe)-Leu-Asp-Ile-Ile-1-Nal;
Ac-D-Tyr(OEt)-Leu-Asp-Ile-Ile-1-Nal;
Ac-D-2-Nal-Leu-Asp-Ile-Ile-1-Nal;
Ac-D-1-Nal-Leu-Asp-Ile-Ile-1-Nal;
Ac-D-Dip-Leu-Asp-Ile-Ile-1-Nal;
Ac-D-Bip-Leu-Asp-Ile-Ile-1-Nal;
Ac-D-His-Leu-D-Asp-Ile-D-Ile-Trp;
Ac-D-Phe-Leu-D-Asp-Ile-D-Ile-Trp;
Ac-D-Bip-Leu-D-Asp-Ile-D-Ile-Trp;
Ac-D-Dip-Leu-D-Asp-Ile-D-Ile-Trp;
Ac-D-2-Nal-Leu-D-Asp-Ile-D-Ile-Trp;
Ac-D-1-Nal-Leu-D-Asp-Ile-D-Ile-Trp;
Ac-D-Trp-Leu-D-Asp-Ile-D-Ile-Trp;
Ac-D-Dip -Asn-Ile-Ile-Trp;
Ac-D-Dip-Phe-Ile-Ile-Trp;
Ac-D-Dip-Ile-Ile-Trp;
Ac-D-Dip-Asp-Ile-Ile-Trp;
Ac-D-N-MeDip-Leu-Asp-Ile-Ile-Trp;
Ac-D-Dip-Leu-Asp-Ile-Ile-N-MeTrp;
Ac-D-Dip-Leu-Asp-Ile-N-MeIle-Trp;
Ac-D-Dip-Leu-Asp-N-MeIle-Ile-Trp;
Ac-D-Dip-Leu-N-MeAsp-Ile-Ile-Trp;
Ac-D-Dip-N-MeLeu-Asp-Ile-Ile-Trp;
Ac-D-Phe-Asp-Ile-Ile-Trp;
Ac-D-His-Asp-Ile-Ile-Trp;
Ac-D-Trp-Asp-Ile-Ile-Trp;
Ac-D-Tyr-Asp-Ile-Ile-Trp;
Ac-D-Tyr(OMe)-Asp-Ile-Ile-Trp;
Ac-D-Tyr(OEt)-Asp-Ile-Ile-Trp;
Ac-D-2-Nal-Asp-Ile-Ile-Trp;
Ac-D-1-Nal-Asp-Ile-Ile-Trp;
Ada-D-Phe-Asp-Ile-Ile-Trp;
Ada-D-His-Asp-Ile-Ile-Trp;
Ada-D-Trp-Asp-Ile-Ile-Trp;
Ada-D-Tyr-Asp-Ile-Ile-Trp;
Ada-D-Tyr(OMe)-Asp-Ile-Ile-Trp;
Ada-D-Tyr(OEt)-Asp-Ile-Ile-Trp;
Ada-D-2-Nal-Asp-Ile-Ile-Trp;
Ada-D-1-Nal-Asp-Ile-Ile-Trp;
Ada-D-Dip-Asp-Ile-Ile-Trp;
Ada-D-Bip-Asp-Ile-Ile-Trp;
Ac-D-Phe-Asp-Ile-Ile-2-Nal;
Ac-D-Phe-Asp-Ile-Ile-1-Nal;
Ac-D-His-Asp-Ile-Ile-2-Nal;
Ac-D-His-Asp-Ile-Ile-1-Nal;
Ac-D-Tyr-Asp-Ile-Ile-2-Nal;
Ac-D-Tyr-Asp-Ile-Ile-1-Nal;
Ac-D-Trp-Asp-Ile-Ile-2-Nal;
Ac-D-Trp-Asp-Ile-Ile-1-Nal;
Ac-D-Dip-Asp-Ile-Ile-2-Nal;
Ac-D-Dip-Asp-Ile-Ile-1-Nal;
Ac-D-Bip-Asp-Ile-Ile-2-Nal;
Ac-D-Bip-Asp-Ile-Ile-1-Nal;
Ac-D-Phe-Leu-Asp-Ile-Trp;
Ac-D-His-Leu-Asp-Ile-Trp;
Ac-D-Tyr-Leu-Asp-Ile-Trp;
Ac-D-Dip-Leu-Asp-Ile-Trp;
Ac-D-Trp-Leu-Asp-Ile-Trp;
Ac-D-Phe-Leu-Asp-Ile-Ile-Trp-Gly;
Ac-D-His-Leu-Asp-Ile-Ile-Trp-Gly;
Ac-D-Trp-Leu-Asp-Ile-Ile-Trp-Gly;
Ac-D-Tyr(OMe)-Leu-Asp-Ile-Ile-Trp-Gly;
Ac-D-Tyr(OEt)-Leu-Asp-Ile-Ile-Trp-Gly;
Ac-D-2-Nal-Leu-Asp-Ile-Ile-Trp-Gly;
Ac-D-1-Nal-Leu-Asp-Ile-Ile-Trp-Gly;
Ac-D-Dip-Leu-Asp-Ile-Ile-Trp-Gly;
Ac-D-Bip-Leu-Asp-Ile-Ile-Trp-Gly;
Ac-D-Phe-Leu-Asp-Ile-Ile-Trp-Asp;
Ac-D-His-Leu-Asp-Ile-Ile-Trp-Asp;
Ac-D-Trp-Leu-Asp-Ile-Ile-Trp-Asp;
Ac-D-Tyr(OMe)-Leu-Asp-Ile-Ile-Trp-Asp;
Ac-D-Tyr(OEt)-Leu-Asp-Ile-Ile-Trp-Asp;
Ac-D-2-Nal-Leu-Asp-Ile-Ile-Trp-Asp;

Ac-D-1-Nal-Leu-Asp-Ile-Ile-Trp-Asp;
Ac-D-Dip-Leu-Asp-Ile-Ile-Trp-Asp;
Ac-D-Dip-Leu-Asp-Ile-Ile-Trp-NH$_2$;
Ac-D-His-Leu-Asp-Ile-Ile-Trp;
Bppa-Leu-Asp-Ile-Ile-Trp;
Ada-D-Phe-Leu-Asp-Ile-Ile-Trp;
Fmoc-D-Dip-Leu-Asp-Ile-Ile-Trp;
Et-D-Dip-Leu-Asp-Ile-Ile-Trp;
Bz-D-Dip-Leu-Asp-Ile-Ile-Trp;
Pya-D-Dip-Leu-Asp-Ile-Ile-Trp;
Cxl-D-Dip-Leu-Asp-Ile-Ile-Trp;
Ada-D-Dip-Leu-Asp-Ile-Ile-Trp;
Cxl(U)-D-Dip-Leu-Asp-Ile-Ile-Trp;
Me(U)-D-Dip-Leu-Asp-Ile-Ile-Trp;
tBu-D-Dip-Leu-Asp-Ile-Ile-Trp;
CF$_3$CO-D-Dip-Leu-Asp-Ile-Ile-Trp;
Ac-D-Chx-Leu-Asp-Ile-Ile-Trp;
Ac-D-Dopa-Leu-Asp-Ile-Ile-Trp;
D-Pmp-Leu-Asp-Ile-Ile-Trp;
Ac-D-Prop-Leu-Asp-Ile-Ile-Trp;
D-Ana-Leu-Asp-Ile-Ile-Trp;
Ac-D-Ana-Leu-Asp-Ile-Ile-Trp;
Ac-D-Adm-Leu-Asp-Ile-Ile-Trp;
Ac-D-Phe-Ala-Asp-Ile-Ile-Trp;
Ac-D-Phe-Phe-Asp-Ile-Ile-Trp;
Ac-D-Phe-D-Phe-Asp-Ile-Ile-Trp;
Ac-D-Dip-D-Phe-Asp-Ile-Ile-Trp;
D-Dip-Leu-Asn-Ile-Ile-Trp;
Ac-D-Dip-Leu-Tyr-Ile-Ile-Trp;
Ac-D-Phe-Leu-Asp-Ala-Ile-Trp;
Ac-D-Dip-Leu-Asp-Glu-Ile-Trp;
Ac-D-Dip-Leu-Asp-Phe-Ile-Trp;
Ac-D-Dip-Leu-Asp-N-MeIle-Ile-Trp;
Ac-D-Dip-Leu-Asp-Lys-Ile-Trp;
Ac-D-Dip-Leu-Asp-Ala-Ile-Trp;
Ac-D-Phe-Leu-Asp-Ile-Ala-Trp;
Ac-D-Dip-Leu-Asp-Ile-Lys-Trp;
Ac-D-Dip-Leu-Asp-Ile-Phe-Trp;
Ac-D-Dip-Leu-Asp-Ile-Leu-Trp;
Ac-D-Dip-Leu-Asp-Ile-Ile-Phe;
Ac-D-Dip-Leu-Asp-Ile-Ile-Tyr;
Ac-D-Phe-Leu-Asp-Ile-Ile-Tyr;
Ac-D-Phe-Leu-Asn-Pro-Ile-Trp;
Ac-D-Phe-Leu-Asp-Ala-Ile-Tyr;
Ac-D-Dip-Leu-Asn-Pro-Ile-Trp;
Ac-D-Phe-Asp-Phe-Ile-Trp;
D-Dip-Tyr-Ile-Ile-Trp;
Ac-D-Dip-Apa-Ile-Ile-Trp;
Ac-D-Dip-D-Dip-Asp-Ile-Trp; and
Ac-D-Dip-Ahp-Ile-Ile-Trp;
or a pharmaceutically acceptable acid or base addition salt thereof.

The compounds of Formula I are valuable antagonists of endothelin. The tests employed indicate that compounds of Formula I possess endothelin antagonist activity.

Rat Heart Ventricle Binding Assay

Thus, the compounds of Formula I were tested for their ability to inhibit [$^{125}$I]-ET-1([$^{125}$I]-Endothelin-1) binding in a receptor assay. The binding of the compounds of Formula I is determined by incubation (37° C., 2 hours) of a compound of Formula I with [$^{125}$I]-ET-1 and the tissue (rat heart ventricle (10 µg)) in 50 mM Tris(hydroxymethyl) aminomethane hydrochloride (Tris-HCl) (pH 7.4), 5 mM ethylenediamine tetraacetic acid (EDTA), 2 mM ethylene glycol bis(β-aminoethyl ether)N,N,N',N'-tetraacetic acid (EGTA), 100 µM phenylmethylsulfonyl fluoride (PMSF), and 100 µM bacitracin containing protease inhibitors (total volume of 0.5 mL). IC$_{50}$ values are calculated by weighing nonlinear regression curve-fitting to the mass-action (Langmuir) equation.

Endothelin Receptor Binding Assay-A (ET$_A$)

Intact Cell Binding of [$^{125}$I]-ET-1

Materials and Terms Used

Cells

The cells used were rabbit renal artery vascular smooth muscle cells grown in a 48-well dish (1 cm$^2$) (confluent cells).

Growth Media

The growth media was Dulbeccos Modified Eagles/Ham's F12 which contained 10% fetal bovine serum and antibiotics (penicillin/streptomycin/fungizone).

Assay Buffer

The assay buffer was a medium 199 containing Hank's salts and 25 mM Hepes buffer (Gibco 380-2350AJ), supplemented with penicillin/streptomycin/fungizone (0.5%) and bovine serum albumin (1 mg/mL).

[$^{125}$I]-ET-1

Amersham radioiodinated endothelin-1 [$^{125}$I]-ET-1 was used at final concentration of 20,000 cpm/0.25 mL (25 pM).

Protocol

First, add 0.5 mL warm assay buffer (described above) to the aspirated growth media and preincubate for 2 to 3 hours in a 37° C. water bath (do not put back in the 5% carbon dioxide). Second, remove the assay buffers, place the dish on ice, and add 150 µL of cold assay buffer described above to each well. Third, add 50 mL each of cold [$^{125}$I]-ET-1 and competing ligand to the solution (at the same time if possible). Next, place dish in a 37° C. water bath for about 2 hours and gently agitate the dish every 15 minutes. Discard the radioactive incubation mixture in the sink and wash wells 3 times with 1 mL of cold phosphate buffered saline. Last, add 250 mL of 0.25M sodium hydroxide, agitate for 1 hour on rotator, and then transfer the sodium hydroxide extract to gamma counting tubes and count the radioactivity.

Endothelin Receptor Binding Assay-B (ET$_B$)

[$^{125}$I]-ET-1 Binding in Rat Cerebellar Membranes

Materials and Terms Used

Tissue Buffer

The tissue is made up of 20 mM tris(hydroxymethyl) aminomethane hydrochloride (Trizma) buffer, 2 mM ethylenediaminetetraacetate, 100 µM phenylmethylsulfonyl fluoride.

Tissue Preparation

First, thaw one aliquot of frozen rat cerebellar membranes (2 mg protein in 0.5 mL). Next, add 0.5 mL membrane aliquot to 4.5 mL cold tissue buffer, polytron at 7,500 revolutions per minute for 10 seconds. Finally, dilute tissue suspension 1/100 (0.1 mL suspension+9.9 mL tissue buffer), polytron again, and place ice.

Dilution Buffer

Medium 199 with Hank's salts plus 25 mM Hepes+1 mg/mL bovine serum albumin.

[$^{125}$I]-ET-1

Amersham [$^{125}$I]-ET-1 (aliquots of 2×10$^6$ cpm per 100 mL aliquot of [$^{125}$I]-ET-1 with 5.2 mL dilution buffer, place on ice until use (final concentration will be 20,000 cpm per tube, or 25 pM).

Protocol

Add 50 µL each of cold [$^{125}$I]-ET-1 and competing ligand to tubes on ice. Mix in 150 µL of tissue to each tube, vortex briefly, then tap to force all liquids to bottom (total assay volume=250 µL). Then place the tubes in a 37° C. water bath for 2 hours.

Add 2.5 mL cold water buffer (50 mM Trizma buffer) to each tube, filter, and then wash tube with additional 2.5 mL wash buffer and add to filter. Finally, wash filters with an additional 2.5 mL of cold wash buffer.

Count filters for radioactivity in gamma counter.

Inositol Phosphate Accumulation

The functional activity of compounds of Formula I is determined in Rat-1 cells by measuring intracellular levels of second messengers. Thus, cells were prelabeled with [$^3$H]-inositol and endothelin-stimulated accumulation of total [$^3$H]-inositol phosphates in the presence of Li$^+$ is monitored using anion exchange chromatography as described by Muldoon, L. L., et al, *Journal of Biological Chemistry*, Volume 264, pages 8529–8536 (1989) and Dudley, D. T., et al, *Molecular Pharmacology*, Volume 38, pages 370–377 (1990). Antagonist activity is assessed as the ability of added compounds to reduce endothelin-stimulated inositol phosphate accumulation.

Arachidonic Acid Release Assay

Antagonist activity was also measured by the ability of added compounds to reduce endothelin-stimulated arachidonic acid release (AAR) in cultured vascular smooth muscle cells as described in Reynolds, E., Mok, L., *FASEB J.*, 1991, 5, A1066.

Briefly, antagonist activity is measured by the ability of added compounds to reduce endothelin-stimulated arachidonic acid release in cultured vascular smooth muscle cells as arachidonic acid release. [$^3$H] Arachidonic Acid Loading Media (LM) is DME/F12+0.5% FCS×0.25 mCi/mL [$^3$H] arachidonic acid (Amersham). Confluent monolayers of cultured rabbit renal artery vascular smooth muscle cells were incubated in 0.5 mL of the LM over 18 hours, at 37° C., in 5% $CO_2$. The LM was aspirated and the cells were washed once with the assay buffer (Hank's BSS+10 mM HEPES+fatty acid-free BSA (1 mg/mL), and incubated for 5 minutes with 1 mL of the prewarmed assay buffer. This solution was aspirated, followed by an additional 1 mL of prewarmed assay buffer, and further incubated for another 5 minutes. A final 5-minute incubation was carried out in a similar manner. The same procedure was repeated with the inclusion of 10 µL of the test compound (1 nM to 1 µM) and 10 µL ET-1 (0.3 nM) and the incubation was extended for 30 minutes. This solution was then collected, 10 µL of scintillation cocktail was added, and the amount of [$^3$H] arachidonic acid was determined in a liquid scintillation counter.

The data in Table II and IIa below show the endothelin antagonist activity of representative compounds of Formula I.

TABLE II

Biological Activity of Compounds of Formula I

| Example Number | Compound | Binding Assay in Rat Heart Ventricle IC$_{50}$ (µM) or % Inhibition | IP (Inositol Phosphate) Accumulation, IC$_{50}$ (µM) or % Inhibition | IC$_{50}$ (µM) |
|---|---|---|---|---|
| 1 | Ac—D—Phe—Leu—Asp—Ile—Ile—Trp | 0.72 | 0.86 | |
| 4 | D-2-Nal—Leu—Asp—Ile—Ile—Trp | 8.98 | 53% @ 50 µM | |
| 5 | Ac—D-2-Nal—Leu—Asp—Ile—Ile—Trp | 1.63 | 0.63 | 1.9 |
| 6 | Ac—D—Phe—Leu—Asp—Ile—Trp | 24.5 | | |
| 7 | Ac—D—His—Leu—D—Asp—Ile—D—Ile—Trp | 6.03 | | |
| 8 | Ac—D—Phe—Orn—Asp—Ile—Ile—Trp | 0.68 | 0.43 | |
| 9 | Ac—D—Phe—Glu—Asp—Ile—Ile—Trp | 0.74 | | 0.60 |
| 10 | Ac—D—Tyr—Leu—Asp—Ile—Ile—Trp | 0.70 | 0.43 | 0.25 |
| 11 | Ac—D—Phe—Asp—Ile—Ile—Trp | 2.15 | | |
| 12 | Fmoc—D—Phe—Leu—Asp—Ile—Ile—Trp | 0.43 | | |
| 13 | Ac—D—Dip—Leu—Asp—Iled—Ile—Trp | 0.015 | | 0.07 |
| 16 | Ac—D—Dip—Leu—Phe—Ile—Ile—Trp | 0.047 | | 1.8 |
| 17 | Ac—D—Dip—Leu—Asp—Ile—Lys—Trp | 24.6% @ 10 µM | | |
| 18 | Ac—D—Dip—Leu—Asp—Ile—Glu—Trp | 37.0% @ 10 µM | | |
| 19 | Ac—D—Dip—Leu—Asp—Glu—Ile—Trp | 0.015 | | |
| 20 | Ac—D—Dip—Glu—Asp—Ile—Ile—Trp | 0.085 | | |
| 21 | Ac—D—Dip—Orn—Asp—Ile—Ile—Trp | 79% @ 0.05 µM | | 0.02 |
| 23 | Ac—D—Dip—D—Leu—Asp—Ile—Ile—Trp | 41.3% @ 10 µM | | |

TABLE IIa

Biological Activity of Compounds of Formula I

| Example Number | Compound | Binding Assay IC$_{50}$ (µM) or % Inhibition at Receptor Subtypes | | IP (Inositol Phosphate) Accumulation, IC$_{50}$ (µM) or % Inhibition | AAR IC$_{50}$ (µM) |
|---|---|---|---|---|---|
| | | ET$_A$ | ET$_B$ | | |
| 24 | Ac—D—Dip—Leu—Asp—Ile—Ile—Trp—NH$_2$ | 0.32 | 5.0 | | 0.6 |
| 25 | Ac—D—His—Leu—Asp—Ile—Ile—Trp | 9.5 | 10.0 | 1.4 | 3.2 |

TABLE IIa-continued

Biological Activity of Compounds of Formula I

| Example Number | Compound | Binding Assay IC$_{50}$ (μM) or % Inhibition at Receptor Subtypes | | IP (Inositol Phosphate) Accumulation, IC$_{50}$ (μM) or % Inhibition | AAR IC$_{50}$ (μM) |
|---|---|---|---|---|---|
| | | ET$_A$ | ET$_B$ | | |
| 26 | Ac—D—Dip—D—Leu—Asp—Ile—Ile—Trp | 3.0 | 2.0 | | 3.68 |
| 27 | Ac—D—Dip—Leu—Asn—Pro—Ile—Trp | 0.73 | 0.62 | | 8.4 |
| 28 | Bppa—Leu—Asp—Ile—Ile—Trp | 8.0 | 1.7 | | 5.6 |
| 29 | Ada—D—Phe—Leu—Asp—Ile—Ile—Trp | | | 19.7 | |
| 30 | Fmoc—D—Dip—Leu—Asp—Ile—Ile—Trp | 6.0 | 6.0 | | 2.6 |
| 31 | Et—D—Dip—Leu—Asp—Ile—Ile—Trp | 1.8 | 2.0 | | |
| 32 | Bz—D—Dip—Leu—Asp—Ile—Ile—Trp | 4.6 | 0.03 | | |
| 33 | Pya—D—Dip—Leu—Asp—Ile—Ile—Trp | 5.0 | 0.18 | | |
| 34 | Cxl—D—Dip—Leu—Asp—Ile—Ile—Trp | 3.4 | 0.20 | | |
| 35 | Ada—D—Dip—Leu—Asp—Ile—Ile—Trp | 4.0 | 0.5 | | |
| 36 | Cxl(U)—D—Dip—Leu—Asp—Ile—Ile—Trp | 0.82 | 0.05 | | |
| 37 | Me(U)—D—Dip—Leu—Asp—Ile—Ile—Trp | 1.0 | 1.5 | | |
| 38 | tBu—D—Dip—Leu—Asp—Ile—Ile—Trp | 10 | 0.5 | | |
| 39 | CF$_3$CO—D—Dip—Leu—Asp—Ile—Ile—Trp | 0.25 | 0.9 | | |
| 40 | Ac—D—Phe—Leu—Asp—Ile—Ile—Trp | 2.8 | 3.3 | 1.18 | 3.1 |
| 41 | Ac—D—Tyr—Leu—Asp—Ile—Ile—Trp | 0.40 | 7.0 | 0.43 | 0.25 |
| 42 | Ac—D—Chx—Leu—Asp—Ile—Ile—Trp | 2.3 | 1.1 | | |
| 43 | Ac—D—Tyr(OMe)—Leu—Asp—Ile—Ile—Trp | 2.1 | >10 | | 6.2 |
| 44 | 2-D—Nal—Leu—Asp—Ile—Ile—Trp | | | 53% @ 50 μM | |
| 45 | Ac-1-D—Nal—Leu—Asp—Ile—Ile—Trp | 0.30 | 0.45 | | |
| 46 | Ac-2-D—Nal—Leu—Asp—Ile—Ile—Trp | 1.0 | 4.0 | 0.63 | 1.9 |
| 47 | Ac—D—Dopoa—Leu—Asp—Ile—Ile—Trp | 7.0 | >10 | | |
| 48 | Ac—D—Trp—Leu—Asp—Ile—Ile—Trp | 0.13 | 1.8 | | 0.45 |
| 49 | D—Dip—Leu—Asp—Ile—Ile—Trp | 2.1 | 1.9 | 1.92 | |
| 50 | Ac—D—Dip—Leu—Asp—Ile—Ile—Trp | 0.015 | 0.15 | 0.0145 | 0.07 |
| 51 | Ac—D—Bip—Leu—Asp—Ile—Ile—Trp | 4.4 | 3.5 | 6.0 | |
| 52 | D—Pmp—Leu—Asp—Ile—Ile—Trp | 6.0 | 3.87 | | |
| 53 | Ac—D—Pmp—Leu—Asp—Ile—Ile—Trp | 1.5 | 5.5 | | |
| 54 | D—Ana—Leu—Asp—Ile—Ile—Trp | 5.86 | 1.21 | | |
| 55 | Ac—D—Ana—Leu—Asp—Ile—Ile—Trp | 0.54 | 0.79 | | |
| 56 | Ac—D—Adm—Leu—Asp—Ile—Ile—Trp | 3.22 | 1.92 | | |
| 57 | Ac—D—Phe—Glu—Asp—Ile—Ile—Trp | 0.65 | 1.3 | | 0.60 |
| 58 | Ac—D—Phe—Orn—Asp—Ile—Ile—Trp | 0.70 | 4.0 | 0.43 | 2.0 |
| 59 | Ac—D—Phe—Ala—Asp—Ile—Ile—Trp | 0.40 | 0.30 | 0.3 | 0.33 |
| 60 | Ac—D—Phe—Phe—Asp—Ile—Ile—Trp | 0.20 | 0.30 | | 2.6 |
| 61 | Ac—D—Phe—D—Phe—Asp—Ile—Ile—Trp | 0.8 | 0.01 | | 2.7 |
| 62 | Ac—D—Dip—Glu—Asp—Ile—Ile—Trp | 0.025 | 0.052 | | 0.13 |
| 63 | Ac—D—Dip—Orn—Asp—Ile—Ile—Trp | 0.015 | 0.22 | | 0.02 |
| 64 | Ac—D—Dip—D—Phe—Asp—Ile—Ile—Trp | 0.38 | 0.74 | | 0.32 |
| 65 | Ac—D—Dip—N—MeLeu—Asp—Ile—Ile—Trp | 0.20 | 0.60 | | |
| 66 | Ac—D—Dip—Arg—Asp—Ile—Ile—Trp | 0.004 | 0.010 | | |
| 67 | Ac—D—Phe—Leu—Phe—Ile—Ile—Trp | 1.18 | 0.035 | | 4.5 |
| 68 | Ac—D—Dip—Leu—Phe—Ile—Ile—Trp | 1.0 | 0.008 | | 1.8 |
| 69 | Ac—D—Dip—Leu—Lys—Ile—Ile—Trp | 0.48 | 0.033 | | 0.98 |
| 70 | D—Dip—Leu—Asn—Ile—Ile—Trp | 6.43 | 0.833 | | |
| 71 | Ac—D—Dip—Leu—Glu—Ile—Ile—Trp | 0.021 | 0.019 | | 0.43 |
| 72 | Ac—D—Dip—Leu—Tyr—Ile—Ile—Trp | 0.50 | 0.080 | | |
| 73 | Ac—D—Phe—Leu—Asp—Ala—Ile—Trp | 3.50 | 0.33 | | 1.50 |
| 74 | Ac—D—Dip—Leu—Asp—Glu—Ile—Trp | 1.0 | 6.0 | | 0.45 |
| 75 | Ac—D—Dip—Leu—Asp—Chx—Ile—Trp | 0.065 | 0.21 | | 0.15 |
| 76 | Ac—D—Dip—Leu—Asp—Phe—Ile—Trp | 0.11 | 0.05 | | |
| 77 | Ac—D—Dip—Leu—Asp—N—MeIle—Ile—Trp | 0.68 | >1 | | 1.9 |
| 78 | Ac—D—Dip—Leu—Asp—Phe—Ile—Trp | 0.24 | 0.065 | | 0.3 |
| 79 | Ac—D—Dip—Leu—Asp—Lys—Ile—Trp | >10 | 3.7 | | >10 |
| 80 | Ac—D—Dip—Leu—Asp—Ala—Ile—Trp | 0.1 | 0.33 | | 0.42 |
| 81 | Ac—D—Dip—Leu—Asp—Val—Ile—Trp | 0.015 | 0.08 | 0.034 | |
| 82 | Ac—D—Phe—Leu—Asp—Ile—Ala—Trp | 8.0 | >1.0 | | >10 |
| 83 | Ac—D—Dip—Leu—Asp—Ile—Lys—Trp | >10 | 4.2 | | |
| 84 | Ac—D—Dip—Leu—Asp—Ile—Phe—Trp | 4.0 | 7.5 | >10 | |
| 85 | Ac—D—Dip—Leu—Asp—Ile—Leu—Trp | 0.23 | 0.73 | | 0.12 |
| 86 | Ac—D—Dip—Leu—Asp—Ile—Val—Trp | 0.097 | 0.63 | | |
| 87 | Ac—D—Dip—Leu—Asp—Ile—Ile—Phe | 5.0 | 6.8 | | >10 |
| 88 | Ac—D—Dip—Leu—Asp—Ile—Ile—Tyr | 3.7 | 6.3 | | 4.3 |
| 89 | Ac—D—Phe—Leu—Asp—Ile—Ile—Tyr | >10 | 0.22 | | |
| 90 | Ac—D—Phe—Leu—Asn—Pro—Ile—Trp | 1.98 | 2.8 | | 0.11 |
| 91 | Ac—D—Phe—Leu—Asp—Ala—Ile—Tyr | >10 | >10 | | 8.4 |
| 92 | Ac—D—Phe—Asp—Ile—Ile—Trp | 9.1 | 9.3 | 30% @ 10 μM | |
| 93 | Ac—D—Phe—Asp—Phe—Ile—Trp | 37.4% @ 10 μM | 63.7% @ 10 μM | | |
| 94 | Ac—D—Dip—Asp—Ile—Ile—Trp | >1.0 | 0.25 | | 3.2 |
| 95 | D—Dip—Tyr—Ile—Ile—Trp | 8.0 | 0.35 | | 3.90 |

TABLE IIa-continued

Biological Activity of Compounds of Formula I

| Example Number | Compound | Binding Assay IC$_{50}$ (μM) or % Inhibition at Receptor Subtypes | | IP (Inositol Phosphate) Accumulation, IC$_{50}$ (μM) or % Inhibition | AAR IC$_{50}$ (μM) |
|---|---|---|---|---|---|
| | | ET$_A$ | ET$_B$ | | |
| 96 | Ac—D—Dip—Apa—Ile—Ile—Trp | >10 | 3.98 | | >10 |
| 97 | Ac—D—Dip—Leu—Asp—Ile—Trp | 1.5 | 2.1 | | |
| 98 | Ac—D—Dip—D—Dip—Asp—Ile—Trp | 7.87 | >10 | | |
| 99 | Ac—D—Dip—Ahp—Ile—Ile—Trp | 4.09 | 1.86 | | |

In Vitro (Isolated Vessel) Studies

Male New Zealand rabbits were killed by cervical dislocation and exsanguination. Femoral and pulmonary arteries were isolated, cleaned of connective tissue, and cut into 4 mm rings. The endothelium was denuded by placing the rings over hypodermic tubing (32 gauge for femoral rings and 28 gauge for pulmonary rings, Small Parts Inc., Miami, Fla.) and gently rolling them. Denuded rings were mounted in 20 mL organ baths containing Krebs-bicarbonate buffer (composition in mM: NaCl, 118.2; NaHCO$_3$, 24.8; KCl, 4.6; MgSO$_4$, 7.H$_2$O, 1.2; KH$_2$PO$_4$, 1.2; CaCl$_2$.2H$_2$O; Ca—Na$_2$ EDTA, 0.026; Dextrose, 10.0), that was maintained at 37° C., and gassed continuously with 5% CO$_2$ in oxygen (pH 7.4). Resting tension was adjusted to 3.0 g for femoral and 4.0 g pulmonary arteries; the rings were left for 90 minutes to equilibrate. Tension was monitored with force displacement transducers (Grass FT03, Quincy, Mass.) and recorded on a polygraph (Gould 2108, Cleveland, Ohio) recorder.

Vascular rings were tested for a lack of functional endothelium, i.e., lack of an endothelium-dependent relaxation response to carbachol (1.0 μM) in norepinephrine (0.03 μM) contracted rings. Agonist peptides, ET-1, for femoral artery rings and SRTX-6c for pulmonary artery rings (one peptide per experiment), were cumulatively added at 10-minute intervals. In separate experiments, the test compounds (ET antagonists), were added 30 minutes prior to adding the agonist as indicated above.

For the in vitro experiments compounds were dissolved in 0.1% acetic acid in distilled water. The maximum concentration of DMSO in the bath was 0.1% which did not significantly affect developed tension in response to ET-1, ET-3, or SRTX-6c. The antagonist activity of various compounds are expressed as pA$_2$ values in Table III.

were placed in the left carotid artery to measure mean arterial blood pressure (MABP) and left and right jugular veins for drug administration. The trachea was cannulated (PE 240) for artificial respiration (Harvard Apparatus, Model 681, South Natick, Mass.) at a rate of 100 cycles/min and a tidal volume of 3.0 mL/kg. Cardiac output was measured using a thoracic aortic flow probe (Transonics, probe size 1RB, Ithaca, N.Y.).

In separate experiments regional hemodynamics were assessed. To monitor regional blood flow rats were similarly anesthetized and instrumented for measurement of MABP and intravenous (IV) drug administration. The trachea was cannulated and the rats were allowed to breathe spontaneously. In addition, flow probes (Transonics, probe size 1RB, Ithaca, N.Y.) were placed on the left renal, left iliac, right carotid, and/or mesenteric arteries. All rats were ganglionic blocked with mecamylamine (1.25 mg/kg, IV) to block hemodynamic reflexes and allowed to stabilize for 5 minutes.

Responses to rising doses (0.03, 0.1, 0.3, 1.0, and 3.0 nmol/kg, IV bolus) of ET-1 or SRTX-6c were measured continuously and averaged at 1-second intervals during the depressor phase and at 5-second intervals during the pressor phase. Agonists were administered at 5-minute intervals. Changes in SVR and regional vascular resistances were calculated for individual rats based on blood flow and arterial blood pressure measurements at the peak of depressor and pressor responses. The effects of test compounds (ET antagonists) on the hemodynamic responses to ET-1 and S6c were determined in separate experiments. Infusion of the test compounds (1.0 μmol/kg/5 min) were initiated 5 minutes prior to the first ET-1 or SRTX-6c challenge and maintained throughout the agonist dose response curve. Data points for global and regional hemodynamics represent the mean of

| Example Number | Compound | pA$_2$ Values | |
|---|---|---|---|
| | | Rat Femoral Artery | Rat Pulmonary Artery |
| 1 | Ac—D—Dip—Leu—Asp—Ile—Ile—Trp.2Na$^+$ | 6.56 | 6.26 |
| 2 | Ac—D—Dip—Glu—Asp—Ile—Ile—Trp | 6.09 | 6.85 |
| 3 | Ac—D—Dip—Arg—Asp—Ile—Ile—Trp | 6.33 | 5.68 |
| 4 | Ac—D—Dip—Leu—Asp—Phe—Ile—Trp | — | 5.84 |

In Vivo Studies

Male Sprague Dawley rats (300 to 500 g) were anesthetized (Inactin, 120 mg/kg IP) and acutely instrumented for measurement of systemic hemodynamics. Cannulae (PE 50)

four to eight rats. For in vivo experiments compounds were dissolved in 0.1% acetic acid in distilled water.

To determine in vivo endothelin antagonism by Ac-D-Dip-Leu-Asp-Ile-Ile-Trp, male Sprague Dawley rats (300–500 g) were anesthetized (Inactin, 120 mg/kg, IP) and instrumented to measure mean arterial blood pressure, and renal and hind limb blood flow. Ganglionic blockade (mecamylamine, 1.25 mg/kg, IV) was produced to prevent hemodynamic reflexes. ET-1 (0.3–3.0 nM/kg, IV bolus 5 minutes apart) caused transient dose dependent depressor responses followed by slowly (~2 minutes to max.) developing pressure responses. Predominant vasodilator responses to ET-1 were observed in the hind limb versus predominant vasoconstrictor responses in the renal bed. Pretreatment with Ac-D-Dip-Leu-Asp-Ile-Ile-Trp (1.0 μM/kg/5 minutes, IV infusion) significantly attenuated the systemic depressor responses to ET-1, but had no effect on pressor responses. In the regional beds, pretreatment with Ac-D-Dip-Leu-Asp-Ile-Ile-Trp significantly attenuated (~50%) the vasodilatation to ET-1 in the hind limb, whereas the vasoconstriction to ET-1 in the renal bed was unchanged.

As in vivo test bases on the peak effect of single bolus doses of ET antagonists on depressor and pressor responses to ET has been developed in conscious rats. This model is able to provide both potency and duration of action information. Duration of action studies were carried out in the conscious chronically prepared normotensive rats with a 5-day treatment protocol. There were 5 groups of animals with dosing regimen of drug at (10 μM/kg IV bolus) 0, 5, 20, 60, and 120 minutes before the ET-1 challenge. In the control set of animals vehicle was administered instead of drug. There was no repetitive dosing of ET-1 due to the inability to wash out the response. These studies were carried out with the ET antagonist Ac-D-Dip-Leu-Asp-Ile-Ile-Trp. The results indicate that Ac-D-Dip-Leu-Asp-Ile-Ile-Trp showed blocking of the depressor component of the ET-1 challenge 2 hours postdose.

Statistics

An F test for parallelism was used to evaluate the effects of antagonist pretreatment on the contractile activity of ET-1 in isolated vessels. Statistical differences between parallel curves were determined using t-test on $EC_{50}$ values. An F test was used to assess significant differences among treatment groups for systemic and regional hemodynamic parameters.

Paired t-tests, corrected for multiple comparison with the Bonferroni inequality adjustment, were used to determine significant differences from control values within treatment groups.

General Method for Preparing Compounds of Formula I

The compounds of Formula I may be prepared by solid phase peptide synthesis on a peptide synthesizer, for example, an Applied Biosystems 430A peptide synthesizer using activated esters or anhydrides of N-alpha-Boc protected amino acids, on PAM or MBHA resins. Additionally, the compounds of Formula I may also be prepared by conventional solution peptide synthesis. Amino acid side chains are protected as follows: Bzl(Asp, Glu, Ser), 2-Cl-Z(Lys), 2-Br-Z(Tyr), Bom(His), For(Trp), and MeBzl(Cys). Each peptide resin (1.0 g) is cleaved with 9 mL of HF and 1 mL of anisole or p-cresol as a scavenger (60 minutes, 0° C.). The peptide resin is washed with cyclohexane, extracted with 30% aqueous HOAc, followed by glacial HOAc, concentrated under reduced pressure, and lyophilized. (A peptide containing For(Trp) is dissolved in 0° C., the pH is adjusted to 12.5 with 1N KOH (2 minutes), neutralized with glacial HOAc, desalted on $C_{18}$ (as described below), and lyophilized. The crude peptide is purified by preparative reversed phase high performance liquid chromatography (RP-HPLC) on a $C_{18}$ column (2.2×25.0 cm, 15.0 mL/min) with a linear gradient of 0.1% TFA in water to 0.1% TFA in acetonitrile and lyophilized. The homogeneity and composition of the resulting peptide is verified by RP-HPLC, capillary electrophoresis, thin layer chromatography (TLC), proton nuclear magnetic resonance spectrometry (NMR), and fast atom bombardment mass spectrometry (FAB-MS).

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use as antagonist of endothelin, the compounds utilized in the pharmaceutical method of this invention are administered at the initial dosage of about 0.01 mg to about 20 mg per kilogram daily. A daily dose range of about 0.01 mg to about 10 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following nonlimiting examples illustrate the inventors' preferred methods for preparing the compounds of the invention.

EXAMPLE 1

Ac-D-Phe-Leu-Asp-Ile-Ile-Trp

The linear hexapeptide is prepared by standard solid phase synthetic peptide methodology utilizing a Boc/benzyl strategy (Stewart, J. M. and Young, J. D., *Solid Phase Peptide Synthesis*, Pierce Chemical Co., Rockford, Ill., 1984). All protected amino acids and reagents are obtained from commercial sources and are not further purified. The protected peptide resin is prepared on an Applied Biosystems 430A Peptide Synthesizer, utilizing protocols supplied for a dicyclohexylcarbodiimide mediated coupling scheme (Standard 1.0, Version 1.40). Starting with 0.560 g of N-α-Boc-Trp(For)-PAM resin (0.88 meq/g, 0.43 meq of Boc-Trp(For) total) the protected peptide is prepared by the stepwise coupling of the following amino acids (in order of addition): N-α-Boc-D-Phe, N-α-Boc-Leu.$H_2O$, N-α-Boc-Asp(Bzl), and N-α-Boc-Ile.0.5 $H_2O$. A typical cycle for the coupling of an individual amino acid residue is illustrated below (reproduced from the ABI manual):

All the single couple RV cycles conform to the following pattern:

1) 33% TFA in DCM for 80 seconds
2) 50% TFA in DCM for 18.5 minutes
3) Three DCM washes
4) 10% DIEA in DMF for 1 minute
5) 10% DIEA in DMF for 1 minute
6) Five DMF washes
7) Coupling period
8) five DCM washes After the coupling of N-α-Boc-D-Phe, the Boc group is removed with the end-$NH_2$ cycle and the free amine is acetylated with N-acetylimidazole (1.0 g, 120 minutes) in 20 mL of dichloromethane (DCM). The resin is washed with DCM (3×20 mL) and dried under reduced pressure (0.878 g).

The peptide is liberated from the solid support, and the carboxylate of aspartic acid deprotected by treatment with anhydrous hydrogen fluoride (9.0 mL), anisole (1.0 mL), and dimethyl sulfide (0.5 mL) (60 minutes, 0° C.). After removing the hydrogen fluoride under a stream of nitrogen, the resin is washed with diethyl ether (3×30 mL) and extracted with 20% HOAc in water (3×30 mL) and glacial HOAc (2×30 mL). The aqueous extractions are combined, concentrated under reduced pressure, and lyophilized (320 mg). To remove the formyl protecting group, the crude peptide is suspended in 50 mL of aqueous 0.1N KOH at 0° C. for 2 minutes. The pH of the solution is adjusted to less than 4.0 with 10% HCl/$H_2O$ and passed through a C 18 (60 cc) cartridge. The cartridge is washed with $H_2O$ (50 μL), eluted with 0.1% TFA, 70% $CH_3CN$ in $H_2O$, the eluants combined, concentrated under reduced pressure (10 mL), diluted with $H_2O$, and lyophilized to yield 153 mg of a white powder. The crude peptide is dissolved in 4.0 mL of 50% TFA/$H_2O$, filtered through a 0.4 μM syringe filter, and chromatographed on a Vydac 218TP 1022 column (2.2×25.0 cm, 15.0 mL/min, A: 0.1% TFA/$H_2O$, B: 0.1% TFA/$CH_3CN$, Gradient; 0% B for 10 minutes, 10% to 50% B over 120 minutes). Individual fractions are collected and combined based upon analysis by analytical HPLC. The combined fractions are concentrated under reduced pressure (10 mL), diluted with $H_2O$ (50 mL), and lyophilized (14.8 mg). The homogeneity and structure of the resulting peptide is confirmed by analytical HPLC, capillary zone electrophoresis, Proton Nuclear Magnetic Resonance Spectroscopy ($H^1$-E) and Fast Atom Bombardment Mass Spectroscopy (FAB-MS), $MH^+$ 848.4.

In a process analogous to Example 1 using the appropriate amino acids, the corresponding compounds of Formula I are prepared as follows:

EXAMPLE 2

D-2-Nal-Leu-Asp-Ile-Ile-Trp

FAB-MS, $MH^+$ 856.3.

EXAMPLE 3

Ac-D-2-Nal-Leu-Asp-Ile-Ile-Trp

FAB-MS, $MH^+$ 898.5.

EXAMPLE 4

D-1-Nal-Leu-Asp-Ile-Ile-Trp $MH^+$ 856.3, $MNa^+$ 878.2.

EXAMPLE 5

Ac-D-1-Nal-Leu-Asp-Ile-Ile-Trp $MH^+$ 898.5, $MNa^+$ 920.5.

EXAMPLE 6

Ac-D-Phe-Leu-Asp-Ile-Trp $MH^+$ 735.5, $MNa^+$ 757.8.

EXAMPLE 7

Ac-D-His-Leu-D-Asp-Ile-D-Ile-Trp $MH^+$ 838.5, $MNa^+$ 860.40.

EXAMPLE 8

Ac-D-Phe-Orn-Asp-Ile-Ile-Trp $MH^+$ 849.1, $MNa^+$ 871.0.

EXAMPLE 9

Ac-D-Phe-Glu-Asp-Ile-Ile-Trp $MH^+$ 864.1, $MNa^+$ 886.0.

EXAMPLE 10

Ac-D-Tyr-Leu-Asp-Ile-Ile-Trp $MH^+$ 864.0, $MNa^+$ 886.3.

EXAMPLE 11

Ac-D-Phe-Asp-Ile-Ile-Trp $MH^+$ 735.1, $MNa^+$ 757.3.

EXAMPLE 12

Fmoc-D-Phe-Leu-Asp-Ile-Ile-Trp $MH^+$ 1028.1, $MNa^+$ 1050.3.

EXAMPLE 13

Ac-D-Dip-Leu-Asp-Ile-Ile-Trp

FAB-MS, $MNa^+$ 946.6.

EXAMPLE 14

Ac-D-Dip-Ile-Ile-Trp

FAB-MS, $MH^+$ 696.5, $MNa^+$ 718.5.

EXAMPLE 15

Ac-D-Dip-Asp-Ile-Ile-Trp

FAB-MS, $MH^+$ 810.4, $MNa^+$ 833.5.

EXAMPLE 16

Ac-D-Dip-Leu-Phe-Ile-Ile-Trp

FAB-MS, $MNa^+$ 978.3.

EXAMPLE 17

Ac-D-Dip-Leu-Asp-Ile-Lys-Trp

FAB-MS, $MH^+$ 939.6.

EXAMPLE 18

Ac-D-Dip-Leu-Asp-Ile-Glu-Trp

FAB-MS, $MH^+$ 940.9, $MNa^+$ 963.3.

EXAMPLE 19

Ac-D-Dip-Leu-Asp-Glu-Ile-Trp

FAB-MS, $MH^+$ 938.2.

EXAMPLE 20

Ac-D-Dip-Glu-Asp-Ile-Ile-Trp

FAB-MS, $MH^+$ 940.5.

EXAMPLE 21

Ac-D-Dip-Orn-Asp-Ile-Ile-Trp

FAB-MS, $MH^+$ 925.1.

EXAMPLE 22

Ac-D-Dip-Leu-Asp(NMe)-Ile-Ile-Trp

FAB-MS, $MNa^+$ 960.7.

EXAMPLE 23

Ac-D-Dip-D-Leu-Asp-Ile-Ile-Trp

FAB-MS, $MH^+$ 924.12, $M^+Na$ 946.0.

EXAMPLE 24

Disodium salt of Ac-D-Dip-Leu-Asp-Ile-Ile-Trp

A saturated solution of sodium bicarbonate in water is prepared, diluted with water (1:10), chilled to 0° C., and 10 mL of the solution is added to approximately 50 mg of Ac-D-Dip-Leu-Asp-Ile-Ile-Trp (Example 16) with stirring. The pH of the solution is greater than 9. After 10 minutes, the solution is passed through a $C_{18}$ cartridge, washed with water (100 mL), and the absorbed peptide is eluted with methanol (50 mL), concentrated under reduced pressure, resuspended in water (50 mL), and lyophilized (three times) to give the title compound.

Ac-D-Dip-Leu-Asp-Ile-Ile-Trp

FAB-MS, $MH^+$ 924.6, $MNa^+$ 946.6, $M2Na^+$ 968.6.

We claim:

1. A method of treating congestive heart failure and myocardial infarction comprising administering to a host suffering therefrom a therapeutically effective amount of a compound of Formula I $$AA^1-AA^2-AA^3-AA^4-AA^5-AA^6 \quad I$$

wherein $AA^1$ is

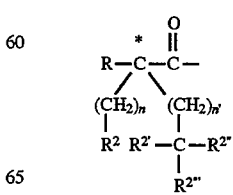

wherein R is hydrogen, alkyl,

wherein $R^3$ and $R^4$ are each the same or different and each is hydrogen, alkyl, alkenyl, alkynyl, cycloalkyl, cycloalkylalkyl, aryl, heteroaryl, or fluorenylmethyl,

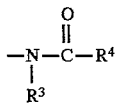

wherein $R^3$ and $R^4$ are each the same or different and each is as defined above,

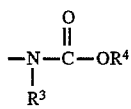

wherein $R^3$ and $R^4$ are each the same or different and each is as defined above,

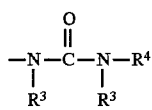

wherein $R^3$ and $R^4$ are defined above, or

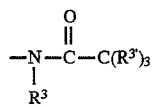

wherein $R^{3'}$ is F, Cl, Br, or I, and $R^3$ is as defined above,
$R^2$ is hydrogen or methyl,
$R^{2'}$, $R^{2''}$, and $R^{2'''}$ are each the same or different and each is hydrogen, alkyl, aryl, or heteroaryl with the proviso that at least one of $R^2$, $R^{2'}$, and $R^{2''}$ is aryl or heteroaryl, and $R^{2'''}$ is hydrogen or methyl,
n is zero, and
n' is zero or an integer of 1, 2, or 3;
$AA^2$ is Apa, Ahp, Dip, D-Phe, Phe, HomoArg, Arg, or

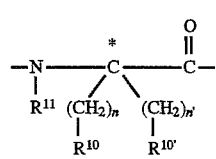

wherein $R^{11}$ is hydrogen or methyl, n is zero, $R^{10}$ is hydrogen or methyl, n' is zero or an integer of 1, 2, 3, 4, or 5, and $R^{10'}$ is alkyl,

wherein $R^{3'}$ and $R^{4'}$ are each the same or different and each is hydrogen, alkyl, or aryl,

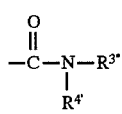

wherein $R^{3'}$ and $R^{4'}$ are as defined above,

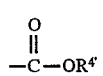

wherein $R^{4'}$ is as defined above;

$-S(O)_m R^{3''}$ wherein m is zero or an integer of 1 of 2 and $R^{3''}$ is as defined above except that $R^{3''}$ is not hydrogen:

$AA^3$ is Lys, Tyr, Phe, or

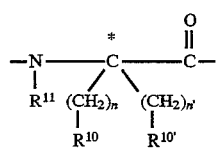

wherein $R^{11}$ is hydrogen or methyl, n is zero, $R^{10}$ is hydrogen or methyl, n'' is zero or an integer of 1, 2, or 3, and $R^{10'}$ is alkyl, aryl,

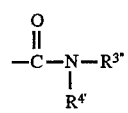

wherein $R^{3''}$ and $R^{4'}$ are as defined above;

wherein $R^{4'}$ is as defined above;
$AA^4$ and $AA^5$ are each Phe, Lys, Glu, Pro, or

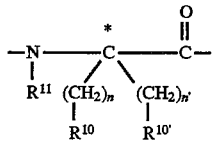

wherein
$R^{11}$ is hydrogen or methyl,
n is zero,
$R^{10}$ is hydrogen or methyl,
n' is zero, and
$R^{10'}$ is alkyl, or cycloalkyl, or one of $AA^2$ or $AA^4$ is absent;
$AA^6$ is

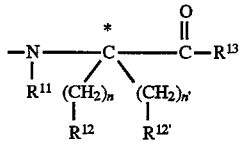

wherein
$R^{11}$ is hydrogen or methyl,
n is zero,
$R^{12}$ is hydrogen, or methyl,
n' is zero or an integer of 1, 2, or 3,
$R^{12'}$ is aryl or heteroaryl,
$R^{13}$ is —$(CH_2)_n$—$CO_2H$ wherein n is zero or an integer of 1, 2, 3, 4, 5, or 6, —$(CH_2)_n$—OH wherein n is zero or an integer of 1, 2, 3, 4, 5, or 6, or

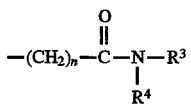

wherein n, $R^3$, and $R^4$ are defined above,

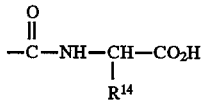

wherein $R^{14}$ is hydrogen or —$CH_2CO_2H$,
stereochemistry at $\overset{*}{c}$ $AA^1$ is D,
stereochemistry at $\overset{*}{c}$ in $AA^2$, $AA^3$, $AA^4$, or $AA^5$ is D or L and stereochemistry at $\overset{*}{c}$ in $AA^6$ is L; with the exclusion of compounds wherein $AA^1$ is

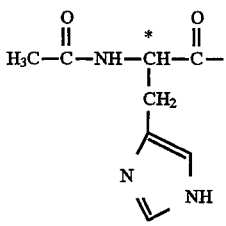

wherein $\overset{*}{c}H$ is D or L stereochemistry, or

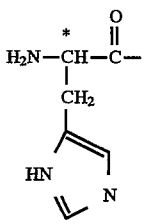

wherein $\overset{*}{c}H$ is D or L stereochemistry,
$AA^2$ is

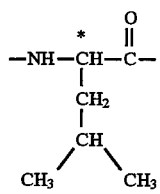

wherein $\overset{*}{c}H$ is D or L stereochemistry,
$AA^3$ is

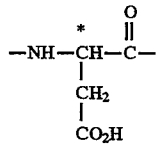

wherein $\overset{*}{c}H$ is D or L stereochemistry,
$AA^4$ and $AA^5$ are each

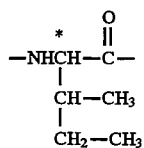

wherein $\overset{*}{c}H$ is D or L stereochemistry, and

AA⁶ is

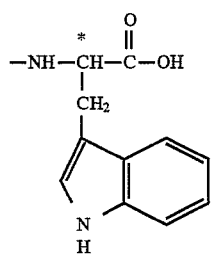

wherein $\overset{*}{\text{C}}$H is D or L stereochemistry but wherein only one of AA¹ or AA² or AA³ or AA⁴ or AA⁵ or AA⁶ are of D-stereochemistry; or a pharmaceutically acceptable salt thereof in unit dosage form.

2. A method of treating subarachnoid hemorrhage comprising administering to a host suffering therefrom a therapeutically effective amount of a compound of Formula I

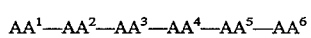    I wherein AA¹ is

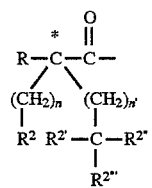

wherein R is hydrogen, alkyl,

wherein R³ and R⁴ are each the same or different and each is hydrogen, alkyl, alkenyl, alkynyl, cycloalkyl, cycloalkylalkyl, aryl, heteroaryl, or fluorenylmethyl,

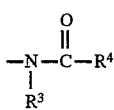

wherein R³ and R⁴ are each the same or different and each is as defined above,

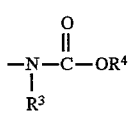

wherein R³ and R⁴ are each the same or different and each is as defined above,

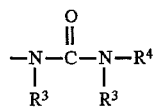

wherein R³ and R⁴ are defined above, or

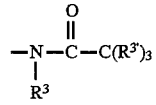

wherein R³' is F, Cl, Br, or I, and R³ is as defined above,

R² is hydrogen or methyl,

R²', R²'', and R²''' are each the same or different and each is hydrogen, alkyl, aryl, or heteroaryl with the proviso that at least one of R², R²', and R²'' is aryl or heteroaryl, and R²''' is hydrogen or methyl, n is zero, and n' is zero or an integer of 1, 2, or 3;

AA² is Apa, Ahp, Dip, D-Phe, Phe, HomoArg, Arg, or

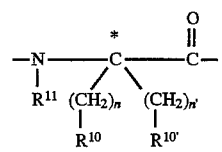

wherein

R¹¹ is hydrogen or methyl, n is zero,

R¹⁰ is hydrogen or methyl, n' is zero or an integer of 1, 2, 3, 4, or 5, and

R¹⁰' is alkyl, OH,

wherein R³'' and R⁴' are each the same or different and each is hydrogen, alkyl, or aryl,

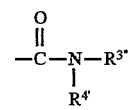

wherein R³'' and R⁴' are as defined above,

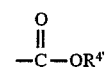

wherein R⁴' is as defined above;

—S(O)ₘR³'' wherein m is zero or an integer of 1 of 2 and R³'' is as defined above except that R³'' is not hydrogen;

AA³ is Lys, Tyr, Phe, or

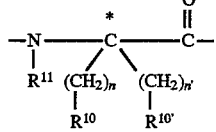

wherein
R¹¹ is hydrogen or methyl,
n is zero,
R¹⁰ is hydrogen or methyl,
n" is zero or an integer of 1, 2, or 3, and
R¹⁰' is alkyl, aryl,

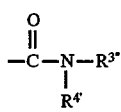

wherein R³" and R⁴' are as defined above;

wherein R⁴' is as defined above;
AA⁴ and AA⁵ are each Phe, Lys, Glu, Pro, or

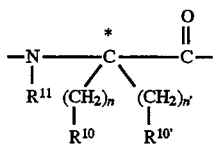

wherein
R¹¹ is hydrogen or methyl,
n is zero,
R¹⁰ is hydrogen or methyl,
n' is zero, and
R¹⁰' is alkyl, or cycloalkyl, or one of AA² or AA⁴ is absent;
AA⁶ is

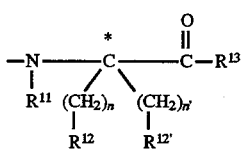

wherein
R¹¹ is hydrogen or methyl,
n is zero,
R¹² is hydrogen, or methyl,
n' is zero or an integer of 1, 2, or 3,
R¹²' is aryl or heteroaryl,
R¹³ is —(CH₂)ₙ—CO₂H wherein n is zero or an integer of 1, 2, 3, 4, 5, or 6, —(CH₂)ₙ—OH wherein n is zero or an integer of 1, 2, 3, 4, 5, or 6, or

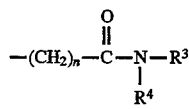

wherein n, R³, and R⁴ are defined above,

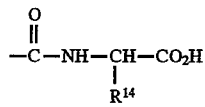

wherein R¹⁴ is hydrogen or —CH₂CO₂H,
stereochemistry at $\overset{*}{C}$ in AA¹ is D,
stereochemistry at $\overset{*}{C}$ in AA², AA³, AA⁴, or AA⁵ is D or L and
stereochemistry at $\overset{*}{C}$ in AA⁶ is L; with the exclusion of compounds wherein AA¹ is

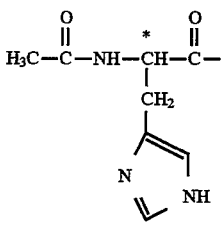

wherein $\overset{*}{C}$H is D or L stereochemistry, or

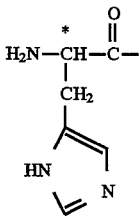

wherein $\overset{*}{C}$H is D or L stereochemistry,
AA² is

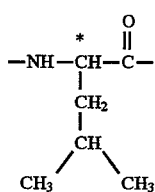

wherein $\overset{*}{C}$H is D or L stereochemistry,
AA³ is

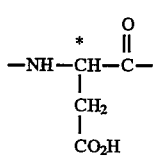

wherein $\overset{*}{C}$H is D or L stereochemistry,

AA⁴ and AA⁵ are each

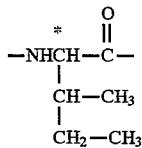

wherein ͕H is D or L stereochemistry, and AA⁶ is

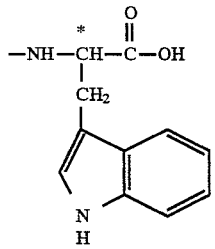

wherein ͕H is D or L stereochemistry but wherein only one of AA¹ or AA² or AA³ or AA⁴ or AA⁵ or AA⁶ are of D-stereochemistry; or a pharmaceutically acceptable salt thereof in unit dosage form.

3. A method of treating preeclampsia comprising administering to a host suffering therefrom a therapeutically effective amount of a compound of Formula I

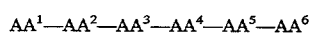

wherein AA¹ is

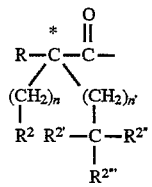

wherein R is hydrogen, alkyl,

wherein R³ and R⁴ are each the same or different and each is hydrogen, alkyl, alkenyl, alkynyl, cycloalkyl, cycloalkylalkyl, aryl, heteroaryl, or fluorenylmethyl,

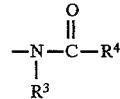

wherein R³ and R⁴ are each the same or different and each is as defined above,

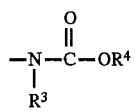

wherein R³ and R⁴ are each the same or different and each is as defined above,

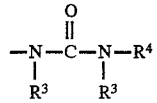

wherein R³ and R⁴ are defined above, or

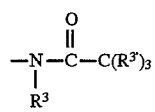

wherein R³' is F, Cl, Br, or I, and R³ is as defined above,
R² is hydrogen or methyl,
R²', R²'', and R²''' are each the same or different and each is hydrogen, alkyl, aryl, or heteroaryl with the proviso that at least one of R², R²', and R²'' is aryl or heteroaryl, and R²''' is hydrogen or methyl,
n is zero, and
n' is zero or an integer of 1, 2, or 3;
AA² is Apa, Ahp, Dip, D-Phe, Phe, HomoArg, Arg, or

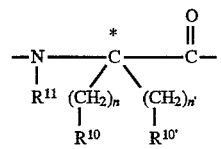

wherein
R¹¹ is hydrogen or methyl,
n is zero,
R¹⁰ is hydrogen or methyl,
n' is zero or an integer of 1, 2, 3, 4, or 5, and
R¹⁰' is alkyl, OH,

wherein R³'' and R⁴' are each the same or different and each is hydrogen, alkyl, or aryl,

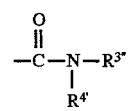

wherein R³'' and R⁴' are as defined above,

wherein R⁴' is as defined above;

—S(O)$_m$R$^{3"}$ wherein m is zero or an integer of 1 of 2 and R$^{3"}$ is as defined above except that R$^{3"}$ is not hydrogen;

AA$^3$ is

Lys,

Tyr,

Phe, or

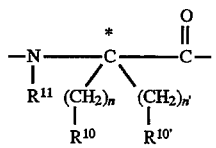

wherein

R$^{11}$ is hydrogen or methyl, n is zero,

R$^{10}$ is hydrogen or methyl, n" is zero or an integer of 1, 2, or 3, and

R$^{10'}$ is alkyl, aryl,

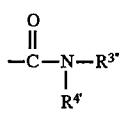

wherein R$^{3"}$ and R$^{4'}$ are as defined above;

wherein R$^{4'}$ is as defined above;

AA$^4$ and AA$^5$ are each

Phe,

Lys,

Glu,

Pro, or

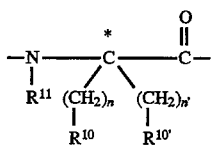

wherein

R$^{11}$ is hydrogen or methyl, n is zero,

R$^{10}$ is hydrogen or methyl, n' is zero, and

R$^{10'}$ is alkyl, or cycloalkyl, or one of AA$^2$ or AA$^4$ is absent;

AA$^6$ is

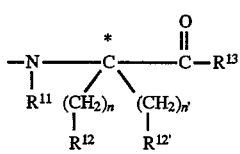

wherein

R$^{11}$ is hydrogen or methyl, n is zero,

R$^{12}$ is hydrogen, or methyl, n' is zero or an integer of 1, 2, or 3,

R$^{12'}$ is aryl or heteroaryl,

R$^{13}$ is —(CH$_2$)$_n$—CO$_2$H wherein n is zero or an integer of 1, 2, 3, 4, 5, or 6, —(CH$_2$)$_n$—OH wherein n is zero or an integer of 1, 2, 3, 4, 5, or 6, or

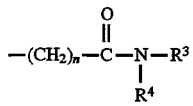

wherein n, R$^3$, and R$^4$ are defined above,

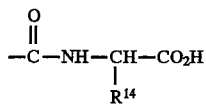

wherein R$^{14}$ is hydrogen or —CH$_2$CO$_2$H, stereochemistry at $\overset{*}{c}$ in AA$^1$ is D, stereochemistry at $\overset{*}{c}$ in AA$^2$, AA$^3$, AA$^4$, or AA$^5$ is D or L and stereochemistry at $\overset{*}{c}$ in AA$^6$ is L; with the exclusion of compounds wherein AA$^1$ is

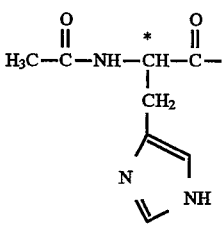

wherein $\overset{*}{c}$H is D or L stereochemistry, or

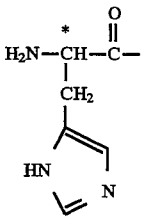

wherein $\overset{*}{c}$H is D or L stereochemistry,

AA$^2$ is

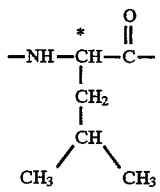

wherein $\overset{*}{c}$H is D or L stereochemistry,

AA³ is

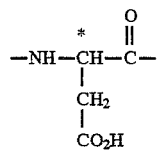

wherein ᶜH is D or L stereochemistry, AA⁴ and AA⁵ are each

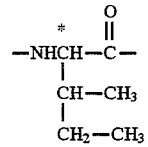

wherein ᶜH is D or L stereochemistry, and AA⁶ is

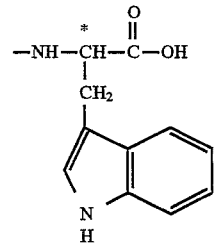

wherein ᶜH is D or L stereochemistry but wherein only one of AA¹ or AA² or AA³ or AA⁴ or AA⁵ or AA⁶ are of D-stereochemistry; or a pharmaceutically acceptable salt thereof in unit dosage form.

4. A method of treating ischemic disease comprising administering to a host suffering therefrom a therapeutically effective amount of a compound of Formula I

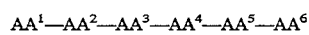

wherein AA¹ is

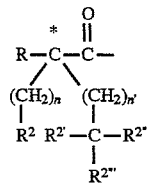

wherein R is hydrogen, alkyl,

wherein $R^3$ and $R^4$ are each the same or different and each is hydrogen, alkyl, alkenyl, alkynyl, cycloalkyl, cycloalkylalkyl, aryl, heteroaryl, or fluorenylmethyl,

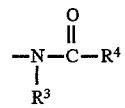

wherein $R^3$ and $R^4$ are each the same or different and each is as defined above,

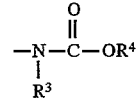

wherein $R^3$ and $R^4$ are each the same or different and each is as defined above,

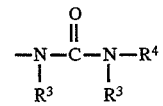

wherein $R^3$ and $R^4$ are defined above, or

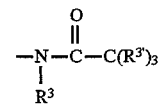

wherein $R^{3'}$ is F, Cl, Br, or I, and $R^3$ is as defined above, $R^2$ is hydrogen or methyl, $R^{2'}$, $R^{2''}$, and $R^{2'''}$ are each the same or different and each is hydrogen, alkyl, aryl, or heteroaryl with the proviso that at least one of $R^2$, $R^{2'}$, and $R^{2''}$ is aryl or heteroaryl, and $R^{2'''}$ is hydrogen or methyl, n is zero, and n' is zero or an integer of 1, 2, or 3;

AA² is Apa, Ahp, Dip, D-Phe, Phe, HomoArg, Arg, or

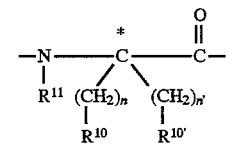

wherein $R^{11}$ is hydrogen or methyl, n is zero, $R^{10}$ is hydrogen or methyl.

n' is zero or an integer of 1, 2, 3, 4, or 5, and $R^{10'}$ is alkyl, OH,

wherein $R^{3''}$ end $R^{4'}$ are each the same or different and each is hydrogen, alkyl, or aryl,

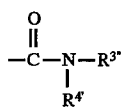

wherein $R^{3''}$ and $R^{4'}$ are as defined above,

wherein $R^{4'}$ is as defined above;

—$S(O)_m R^{3''}$ wherein m is zero or an integer of 1 of 2 and $R^{3''}$ is as defined above except that $R^{3''}$ is not hydrogen;

$AA^3$ is Lys, Tyr, Phe, or

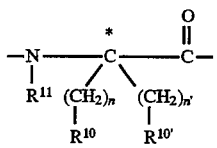

wherein $R^{11}$ is hydrogen or methyl, n is zero, $R^{10}$ is hydrogen or methyl, n" is zero or an integer of 1, 2, or 3 and $R^{10'}$ is alkyl, aryl,

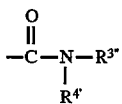

wherein $R^{3''}$ and $R^{4'}$ are as defined above;

wherein $R^{4'}$ is as defined above;

$AA^4$ and $AA^5$ are each Phe, Lys, Glu, Pro, or

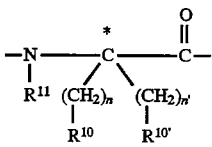

wherein $R^{11}$ is hydrogen or methyl, n is zero, $R^{10}$ is hydrogen or methyl, n' is zero, and $R^{10'}$ is alkyl, or cycloalkyl, or one of $AA^2$ or $AA^4$ is absent;

$AA^6$ is

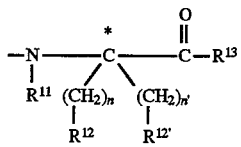

wherein R11 is hydrogen or methyl, n is zero, $R^{12}$ is hydrogen, or methyl, n' is zero or an integer of 1, 2, or 3, $R^{12'}$ is aryl or heteroaryl, $R^{13}$ is —$(CH_2)_n$—$CO_2H$ wherein n is zero or an integer of 1, 2, 3, 4, 5, or 6, —$(CH_2)_n$—OH wherein n is zero or an integer of 1, 2, 3, 4, 5, or 6, or

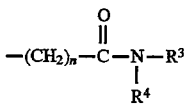

wherein n, $R^3$, and $R^4$ are defined above,

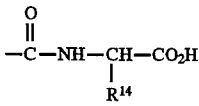

wherein $R^{14}$ is hydrogen or —$CH_2CO_2H$, stereochemistry at $\overset{*}{C}$ in $AA^1$ is D, stereochemistry at $\overset{*}{C}$ in $AA^2$, $AA^3$, $AA^4$, or $AA^5$ is D or L and stereochemistry at $\overset{*}{C}$ in $AA^6$ is L; with the exclusion of compounds wherein $AA^1$ is

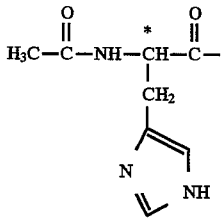

wherein $\overset{*}{C}H$ is D or L stereochemistry, or

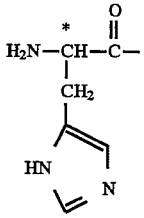

wherein $\overset{*}{C}H$ is D or L stereochemistry,

AA² is

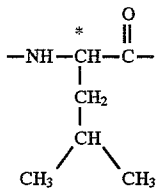

wherein ⁎H is D or L stereochemistry,

AA³ is

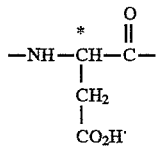

wherein ⁎H is D or L stereochemistry,

AA⁴ and AA⁵ are each

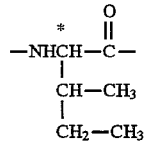

wherein ⁎H is D or L stereochemistry, and
AA⁶ is

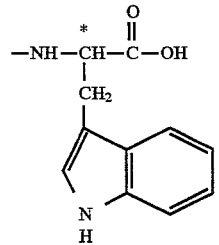

wherein ⁎H is D or L stereochemistry but wherein only one of AA¹ or AA² or AA³ or AA⁴ or AA⁵ or AA⁶ are of D-stereochemistry; or a pharmaceutically acceptable salt thereof in unit dosage form.

5. A method of treating atherosclerosis disorders including Raynaud's disease comprising administering to a host suffering therefrom a therapeutically effective amount of a compound of Formula I $$AA^1{-}AA^2{-}AA^3{-}AA^4{-}AA^5{-}AA^6 \qquad I$$

wherein AA¹ is

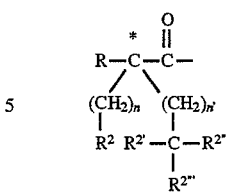

wherein R is hydrogen, alkyl,

wherein $R^3$ and $R^4$ are each the same or different and each is hydrogen, alkyl, alkenyl, alkynyl, cycloalkyl, cycloalkylalkyl, aryl, heteroaryl, or fluorenylmethyl,

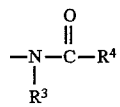

wherein $R^3$ and $R^4$ are each the same or different and each is as defined above,

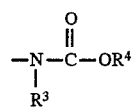

wherein $R^3$ and $R^4$ are each the same or different and each is as defined above,

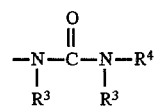

wherein $R^3$ and $R^4$ are defined above, or

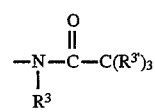

wherein $R^{3'}$ is F, Cl, Br, or I, and $R^3$ is as defined above,
$R^2$ is hydrogen or methyl,
$R^{2'}$, $R^{2''}$, and $R^{2'''}$ are each the same or different and each is hydrogen, alkyl, aryl, or heteroaryl with the proviso that at least one of $R^2$, $R^{2'}$, and $R^{2''}$ is aryl or heteroaryl, and $R^{2'''}$ is hydrogen or methyl,
n is zero, and
n' is zero or an integer of 1, 2, or 3;
AA² is Apa, Ahp, Dip, D-Phe, Phe, HomoArg, Arg, or

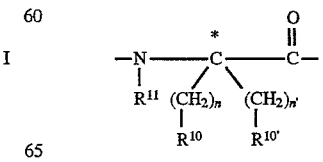

wherein $R^{11}$ is hydrogen or methyl, n is zero, $R^{10}$ is hydrogen or methyl, n' is zero or an integer of 1, 2, 3, 4, or 5, and $R^{10'}$ is alkyl, OH

wherein $R^{3''}$ and $R^{4'}$ are each the same or different and each is hydrogen, alkyl, or aryl,

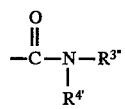

wherein $R^{3''}$ and $R^{4'}$ are as defined above,

wherein $R^{4'}$ is as defined above;

—$S(O)_m R^{3''}$ wherein m is zero or an integer of 1 of 2 and $R^{3''}$ is as defined above except that $R^{3''}$ is not hydrogen;

$AA^3$ is Lys, Tyr, Phe, or

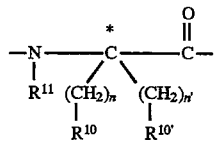

wherein $R^{11}$ is hydrogen or methyl, n is zero, $R^{10}$ is hydrogen or methyl, n" is zero or an integer of 1, 2, or 3, and $R^{10'}$ is alkyl, aryl,

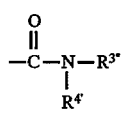

wherein $R^{3''}$ and $R^{4'}$ are as defined above;

wherein $R^{4'}$ is as defined above;

$AA^4$ and $AA^5$ are each Phe, Lys, Glu, Pro, or

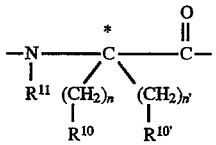

wherein $R^{11}$ is hydrogen or methyl, n is zero, $R^{10}$ is hydrogen or methyl, n' is zero, and $R^{10'}$ is alkyl, cycloalkyl, or one of $AA^2$ or $AA^4$ is absent;

$AA^6$ is

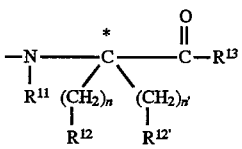

wherein $R^{11}$ is hydrogen or methyl, n is zero, $R^{12}$ is hydrogen., or methyl, n' is zero or an integer of 1, 2, or 3, $R^{12'}$ is aryl or heteroaryl, $R^{13}$ is —$(CH_2)_n$—$CO_2H$ wherein n is zero or an integer of 1, 2, 3, 4, 5, or 6, —$(CH_2)_n$—OH wherein n is zero or an integer of 1, 2, 3, 4, 5, or 6, or

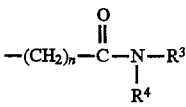

wherein n, $R^3$, and $R^4$ are defined above,

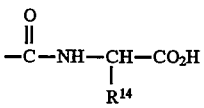

wherein $R^{14}$ is hydrogen or —$CH_2CO_2H$, stereochemistry at $\overset{*}{C}$ in $AA^1$ is D, stereochemistry at $\overset{*}{C}$ in $AA^2$, $AA^3$, $AA^4$, or $AA^5$ is D or L and stereochemistry at $\overset{*}{C}$ in $AA^6$ is L; with the exclusion of compounds wherein $AA^1$ is

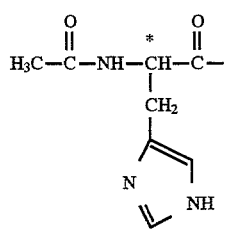

wherein ⁎cH is D or L stereochemistry, or

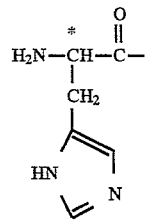

wherein ⁎cH is D or L stereochemistry,
AA² is

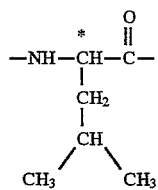

wherein ⁎cH is D or L stereochemistry,

AA³ is

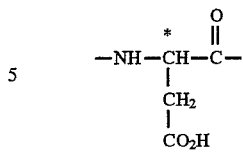

wherein ⁎cH is D or L stereochemistry, AA⁴ and AA⁵ are each

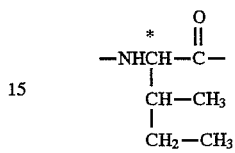

wherein ⁎cH is D or L stereochemistry, and AA⁶ is

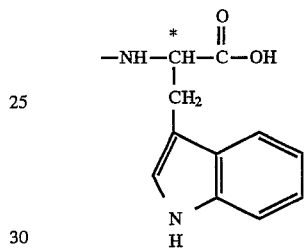

wherein ⁎cH is D or L stereochemistry but wherein only one of AA¹ or AA² or AA³ or AA⁴ or AA⁵ or AA⁶ are of D-stereochemistry; or a pharmaceutically acceptable salt thereof in unit dosage form.

* * * * *

UNITED STATES PATENT AND TRADEMARK OFFICE
CERTIFICATE OF CORRECTION

PATENT NO. : 5,641,752

DATED : June 24, 1997

INVENTOR(S) : Wayne Livingston Cody, Patricia DePue, Marian Doherty, Xiaoqiang He, Douglas Taylor It is certified that error appears in the above-identified patent and that said Letters Patent is hereby corrected as shown below:

Column 50, line 8, insert -- OH, --.

Signed and Sealed this

Eighth Day of February, 2000

Attest:

Q. TODD DICKINSON

*Attesting Officer*

*Commissioner of Patents and Trademarks*